US010295367B2

(12) United States Patent
Sekitani et al.

(10) Patent No.: US 10,295,367 B2
(45) Date of Patent: May 21, 2019

(54) SIGNAL DETECTION DEVICE AND SIGNAL DETECTION METHOD

(71) Applicant: Japan Science and Technology Agency, Kawaguchi-shi, Saitama (JP)

(72) Inventors: Tsuyoshi Sekitani, Tokyo (JP); Takao Someya, Tokyo (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 215 days.

(21) Appl. No.: 14/432,572

(22) PCT Filed: Sep. 30, 2013

(86) PCT No.: PCT/JP2013/076568
§ 371 (c)(1),
(2) Date: Mar. 31, 2015

(87) PCT Pub. No.: WO2014/054586
PCT Pub. Date: Apr. 10, 2014

(65) Prior Publication Data
US 2015/0276430 A1 Oct. 1, 2015

(30) Foreign Application Priority Data
Oct. 2, 2012 (JP) ................................. 2012-220427

(51) Int. Cl.
*A61B 5/04* (2006.01)
*G01D 3/028* (2006.01)
(Continued)

(52) U.S. Cl.
CPC ........... *G01D 3/028* (2013.01); *A61B 5/0478* (2013.01); *A61B 5/04085* (2013.01);
(Continued)

(58) Field of Classification Search
CPC ....... A61B 5/22; A61B 5/0048; A61B 5/0537; A61B 5/04001; A61B 5/0478; A61B 5/6868; A61B 5/6877
(Continued)

(56) References Cited

U.S. PATENT DOCUMENTS 4,125,110 A     11/1978   Hymes
4,274,420 A *   6/1981   Hymes ............... A61B 5/04087
                                                       600/391
(Continued)

FOREIGN PATENT DOCUMENTS

CN    1574368 A    2/2005
CN    1922732 A    2/2007
(Continued)

OTHER PUBLICATIONS

International Search Report received for PCT Patent Application No. PCT/JP2013/076568, of which the present application is a U.S. national phase, dated Oct. 29, 2013, with English Translation, 2 pages.
(Continued)

*Primary Examiner* — Joseph A Stoklosa
*Assistant Examiner* — Brian M Antiskay

(57) ABSTRACT

A signal detection device according to an aspect of the invention includes a laminated structure of a first circuit layer (201) in which a plurality of electrodes brought into contact with a subject is formed, a second circuit layer (202) in which a plurality of amplifiers having an input portion capacitively coupled to the plurality of electrodes, respectively, is formed, and a third circuit layer (203) in which a plurality of transistors for reading outputs of the plurality of amplifiers is formed, an insulation layer which seals the second circuit layer is formed between the plurality of electrodes formed in the first circuit layer and the second
(Continued)

circuit layer, and the plurality of electrodes and the input portions of the plurality of amplifiers are capacitively coupled to each other via the insulation layer.

11 Claims, 13 Drawing Sheets

(51) Int. Cl.
    *A61B 5/0478* (2006.01)
    *G06F 3/044* (2006.01)
    *H01L 23/48* (2006.01)
    *H01L 25/18* (2006.01)
    *A61B 5/0408* (2006.01)
    *A61B 5/00* (2006.01)
    *A61N 1/00* (2006.01)
    *H01L 25/065* (2006.01)
    *H01L 49/02* (2006.01)

(52) U.S. Cl.
    CPC ............ *A61B 5/7203* (2013.01); *G06F 3/044* (2013.01); *H01L 23/48* (2013.01); *H01L 25/18* (2013.01); *A61B 5/0408* (2013.01); *A61B 2562/0209* (2013.01); *H01L 25/0657* (2013.01); *H01L 28/20* (2013.01); *H01L 28/40* (2013.01); *H01L 2224/32145* (2013.01)

(58) Field of Classification Search
    USPC ........ 600/300, 372, 382–393, 544–545, 587, 600/377–378; 607/115–118
    See application file for complete search history.

(56) References Cited

U.S. PATENT DOCUMENTS

| | | | |
|---|---|---|---|
| 4,735,847 A * | 4/1988 | Fujiwara ................. | H01R 4/04 428/209 |
| 9,061,134 B2 * | 6/2015 | Askin, III ............ | A61B 5/0408 |
| 2001/0004495 A1 | 6/2001 | Itoyama et al. | |
| 2002/0120186 A1 | 8/2002 | Keimel | |
| 2006/0129056 A1 | 6/2006 | Leuthardt et al. | |
| 2006/0257645 A1 | 11/2006 | Asaka et al. | |
| 2006/0266981 A1 | 11/2006 | Asaka et al. | |
| 2008/0192407 A1 | 8/2008 | Lu | |
| 2009/0221896 A1 * | 9/2009 | Rickert ................ | A61B 5/0478 600/378 |
| 2010/0145176 A1 * | 6/2010 | Himes ................... | A61B 5/0478 600/378 |
| 2011/0054583 A1 | 3/2011 | Litt | |
| 2012/0228558 A1 | 9/2012 | Konishi et al. | |
| 2013/0041235 A1 * | 2/2013 | Rogers ................. | A61B 5/6867 600/306 |
| 2013/0165353 A1 | 6/2013 | Mazyar et al. | |
| 2015/0224210 A1 | 8/2015 | Sekitani et al. | |

FOREIGN PATENT DOCUMENTS

| | | |
|---|---|---|
| CN | 101693125 A | 4/2010 |
| JP | S54-077489 A | 6/1979 |
| JP | H06-197877 A | 7/1994 |
| JP | H09-158054 A | 6/1997 |
| JP | H09-271466 A | 10/1997 |
| JP | 2001-164419 A | 6/2001 |
| JP | 2004-523665 A | 8/2004 |
| JP | 3676337 B2 | 5/2005 |
| JP | 2005-176428 A | 6/2005 |
| JP | 2005-209736 A | 8/2005 |
| JP | 2006-320484 A | 11/2006 |
| JP | 2006-345295 A | 12/2006 |
| JP | 4038685 B2 | 1/2008 |
| JP | 4134306 B2 | 6/2008 |
| JP | 2008-162899 A | 7/2008 |
| JP | 2008-239468 A | 10/2008 |
| JP | 2009-035619 A | 2/2009 |
| JP | 2010-512298 A | 4/2010 |
| JP | 2010-515779 A | 5/2010 |
| JP | 2008-239468 A | 10/2010 |
| JP | 2011-513038 A | 4/2011 |
| JP | 2012-032358 A | 2/2012 |
| TW | 311949 B | 8/1997 |
| WO | 2002/038860 A2 | 5/2002 |
| WO | 2008/046010 A2 | 4/2008 |
| WO | 2008/070926 A1 | 6/2008 |
| WO | 2009/069605 A1 | 6/2009 |
| WO | 2009/101985 A1 | 8/2009 |
| WO | 2009/102077 A1 | 8/2009 |
| WO | 2011/055776 A1 | 5/2011 |
| WO | 2011/071295 A2 | 6/2011 |
| WO | 2011/084450 A1 | 7/2011 |
| WO | 2014/030556 A1 | 2/2014 |

OTHER PUBLICATIONS

State Intellectual Property Office of People's Republic of China, "Office Action" issued in Chinese Patent Application No. 201380051111.9, which is a Chinese counterpart of U.S. Appl. No. 14/432,572 dated Mar. 3, 2016, 10 pages (5 pages of English Translation of Office Action and 5 pages of Office Action).
Tomoyuki Yokota et al., "Sheet-type Organic Active Matrix Amplifier System using Vth-Tunable, Pseudo-CMOS Circuits with Floating-gate Structure", Electron Devices Meeting (IEDM), 2011 IEEE International, IEEE, Dec. 5, 2011, pp. 14.4.1-14.4.4.
European Patent Office, "Extended European Search Report," issued in European Patent Application No. 13 843 451.9, which is a European counterpart of U.S. Appl. No. 14/432,572, dated May 17, 2016, 7 pages.
United States Patent and Trademark Office, "Office Action", issued in U.S. Appl. No. 14/423,358, dated Nov. 8, 2017, 12 pages.
Isao Tsukagoshi, "Development History of the Anisotropic Conductive Film ANISOLM", Hitachi Chemical Technical Report, Jul. 2003, No. 41, pp. 7-18, <URL:http://www.hitachichem.co.jp/japanese/report/041/41_sou.pdf>.
Tsuyoshi Sekitani et al., "A Rubberlike Strechable Active Matrix Using Elastic Conductors", Science, Sep. 12, 2008, vol. 321, No. 5895, pp. 1468-1472.
Takanori Fukushima et al., "Molecular Ordering of Organic Molten Salts Triggered by Single-Walled Carbon Nanotubes", Science, Jun. 27, 2003, vol. 300, No. 5628, pp. 2072-2074.
Japan Patent Office, "Notice of Reasons for Rejection", issued in Japanese Patent Application No. 2014-539731, which is a Japanese counterpart of U.S. Appl. No. 14/432,572, dated Aug. 8, 2017, 10 pages (5 pages of English translation of Office Action, and 5 pages of Office Action).
Japan Patent Office, "Notice of Reasons for Rejection", issued in Japanese Patent Application No. 2014-531585 which is a Japanese counterpart of U.S. Appl. No. 14/423,358, dated Sep. 26, 2017, 11 pages (6 pages of English translation of Office Action, and 5 pages of Office Action).
Japan Patent Office, "Office Action", issued in Japanese Patent Application No. 2014-531585, dated May 9, 2017, 8 pages (4 pages of English translation of Office Action and 4 pages of Office Action).
State Intellectual Property Office of People's Republic of China, Office Action and Search Report, issued in Chinese Patent Application No. 201380043801, dated Nov. 23, 2015, 7 pages (2 pages of English Translation of Search Report, 3 pages of Office Action and 2 pages of Search Report).
International Search Report received for PCT Patent Application No. PCT/JP2013/071689, dated Oct. 29, 2013 (2 pages of English Translation and 2 pages of PCT search report).
International Preliminary Report on Patentability received for PCT Patent Application No. PCT/JP2013/071689, dated Dec. 16, 2014 (1 page of English Translation and 5 pages of PCT preliminary report).
Jonathan Viventi et al., "Flexible, Foldable, Actively Multiplexed, High-Density Electrode Array for Mapping Brain Activity in vivo", Nature Neuroscience, vol. 14, No. 12, pp. 1599-1607 (2011), Nature America, Inc.

(56) References Cited

OTHER PUBLICATIONS

Quan Qing et al., "Nanowire transistor arrays for mapping neural circuits in acute brain slices", PNAS, vol. 107, No. 5, pp. 1882-1887 (2010).
Hao Zhang et al., "Regenerated-Cellulose/Multiwalled-Carbon-Nanotube Composite Fibers with Enhanced Mechanical Properties Prepared with the Ionic Liquid 1-Allyl-3-methylimidazolium Chloride", Advanced Materials, vol. 19, No. 5, pp. 698-704, XP055079929, ISSN: 0935-9648 (Mar. 5, 2007).
European Patent Office, "Extended European Search Report," issued in European Patent Application No. 13 831 736.7, 9 pages (dated Mar. 21, 2016).
State Intellectual Property Office of People's Republic of China, "Office Action", issued in Chinese Patent Application No. 201380043801.X, dated Oct. 17, 2016, 42 pages (26 pages of English Translation of Office Action and 16 pages of Office Action).
United States Patent and Trademark Office, "Restriction Requirement", issued in U.S. Appl. No. 14/423,358, dated Sep. 26, 2016, 9 pages.
Japan Science and Technology Agency, "Response to Restriction Requirement for U.S. Appl. No. 14/423,358", submitted to United States Patent and Trademark Office dated Nov. 28, 2016, 2 pages.
United States Patent and Trademark Office, "Non-Final Office Action", issued in U.S. Appl. No. 14/423,358, dated Dec. 12, 2016, 10 pages.
Japan Science and Technology Agency, "Response to Non-Final Office Action for U.S. Appl. No. 14/423,358", submitted to United States Patent and Trademark Office dated Jun. 12, 2017, 10 pages.

\* cited by examiner

SIGNAL DETECTION DEVICE AND SIGNAL DETECTION METHOD

CROSS REFERENCE TO RELATED APPLICATIONS

This patent application is a U.S. national stage application under 35 U.S.C. § 371 of International Patent Application No. PCT/JP2013/076568 filed on Sept. 30, 2013, which claims the benefit of foreign priority to Japanese Patent Application No. JP 2012-220427 filed on Oct. 2, 2012. The International Application was published in Japanese on Apr. 10, 2014, as International Publication No. WO 2014/054586 A1 under PCT Article 21(2).

BACKGROUND OF THE INVENTION

Field of the Invention

The present invention relates to a signal detection device and a signal detection method for detecting a signal.

Priority is claimed on Japanese Patent Application No. 2012-220427, filed on Oct. 2, 2012, the content of which is incorporated herein by reference.

Description of Related Art

Hitherto, signal detection devices such as electrocardiographs and electroencephalographs have been known as devices for detecting a biosignal (PTL 1). Usually, in these types of signal detection devices, a differential amplifier amplifies a difference between signals of a pair of electrodes mounted on an organism which is a subject. By taking the difference between the signals, noise components having the same phase, which are included in the respective signals, are canceled and a detection signal having a high signal to noise ratio is obtained.

CITATION LIST

Patent Literature

[PTL 1] Japanese Unexamined Patent Application, First Publication No. H6-197877

SUMMARY OF THE INVENTION

However, according to the above-described prior art, the electrodes and the differential amplifier are connected through wiring cables, and thus noise may be mixed on the wiring cables and there is a limit on the improvement of the signal to noise ratio of the detection signal. In addition, even when the electrodes and the differential amplifier are formed integrally with each other, there is a concern that the environment in a living body may cause a failure or malfunction of an electronic circuit of the amplifier when the electrodes and the differential amplifier formed integrally with each other are embedded over a long period of time in the living body which is a subject. Moreover, since a metal or the like having poor flexibility is used as a material of the electrode, it is difficult to mount the electrode on the surface tissue of a living body such as a heart which beats repeatedly. Even when the electrode can be mounted, the electrode having poor flexibility may inhibit the movement of the heart, and thus it is difficult to accurately detect a biosignal generated from the heart.

The invention is contrived in view of the circumstances, and an object thereof is to provide a signal detection device and a signal detection method adapted to improve a signal to noise ratio of a detection signal and to stably detect a signal generated from a subject without inhibiting the movement of the subject.

Solution to Problem

In order to solve the problem, according to an aspect of the invention, a signal detection device which detects a signal generated from a subject includes a laminated structure of a first circuit layer in which a plurality of electrodes brought into contact with the subject is formed, a second circuit layer in which a plurality of amplifiers having an input portion capacitively coupled to the plurality of electrodes, respectively, is formed, and a third circuit layer in which a plurality of transistors for reading outputs of the plurality of amplifiers is formed, an insulating layer which seals the second circuit layer is formed between the plurality of electrodes formed in the first circuit layer and the second circuit layer, and the plurality of electrodes and the input portions of the plurality of amplifiers are capacitively coupled to each other through the insulating layer.

In the signal detection device, for example, the electrode is made of a conductive material in which a carbon nanomaterial doubly covered with molecules constituting a hydrophilic ionic liquid and a water-soluble polymer is dispersed in a water-soluble polymer medium and the water-soluble polymer is crosslinked.

In the signal detection device, for example, wiring for reading output signals of the plurality of amplifiers formed in the second circuit layer through the plurality of transistors formed in the third circuit layer is drawn to one side of the third circuit layer opposite the other side on which the second circuit layer is positioned.

In the signal detection device, for example, the wiring is drawn to the one side of the third circuit layer in an outer circumferential region of the third circuit layer.

In the signal detection device, for example, a plurality of capacitors is formed in the first circuit layer to capacitively couple the plurality of electrodes formed in the first circuit layer and the input portions of the plurality of amplifiers formed in the second circuit layer.

In the signal detection device, for example, the first circuit layer and the second circuit layer, and the second circuit layer and the third circuit layer, are each electrically connected through an anisotropic conductive sheet.

In the signal detection device, for example, a member constituting the first circuit layer forms a sealing layer which seals the second circuit layer.

In the signal detection device, for example, the second circuit layer is interposed between the first circuit layer and the third circuit layer, and thus the first circuit layer, the second circuit layer, and the third circuit layer are laminated, and the first circuit layer and the third circuit layer have the same bending rigidity.

In order to solve the problem, according to an aspect of the invention, a signal detection method of detecting a signal from the subject by using the signal detection device includes a step of selectively reading output signals of any of the plurality of amplifiers formed in the second circuit layer through the plurality of transistors formed in the third circuit layer.

In the signal detection method, for example, the step of selectively reading output signals of any of the plurality of amplifiers formed in the second circuit layer includes a first step of scanning and sequentially reading output signals of the plurality of amplifiers via the plurality of transistors, a second step of generating a strength distribution of the output signals of the plurality of amplifiers read in the first step, and a third step of simultaneously reading one or more output signals of the plurality of amplifiers specified based on the result of the analysis of the strength distribution.

According to an aspect of the invention, since the electrode and the amplifier are formed integrally with each other, the signal to noise ratio of a detection signal can be improved. According to an aspect of the invention, since the electrode and the input portion of the amplifier are capacitively connected to each other, the amplifier can be sealed when viewed from the electrode, and the influence of the environment in which the electrode is provided on the operation of the amplifier can be suppressed. According to an aspect of the invention, since a signal detection device having an electrode having excellent flexibility can be realized, a signal can be detected from a subject without inhibiting the movement of the subject.

BRIEF DESCRIPTION OF THE DRAWINGS

FIG. 8A is a photograph showing a composition in which carbon nanotubes covered with molecules constituting $DEMEBF_4$ are dispersed in polyrotaxane, FIG. 8B is a photograph of a sheet obtained by photo-crosslinking the composition shown in FIG. 8A, and FIG. 8C is an optical microscope photograph of the composition shown in FIG. 8A, subjected to photo-crosslinking and patterning of a microstructure having a line width of approximately 50 μm.

FIG. 9A is a TEM image of carbon nanotubes which can be used in the invention, FIG. 9B is a TEM image of carbon nanotubes covered with polyrotaxane, obtained by mixing carbon nanotubes and polyrotaxane in water without an ionic liquid and performing fragmentation and stirring with a jet mill, and FIG. 9C is a TEM image of a carbon nanomaterial or a composition obtained under the same conditions as the conditions for manufacturing the composition shown in FIG. 8A.

DETAILED DESCRIPTION OF THE INVENTION

[Description of Configuration]

Figure 1:
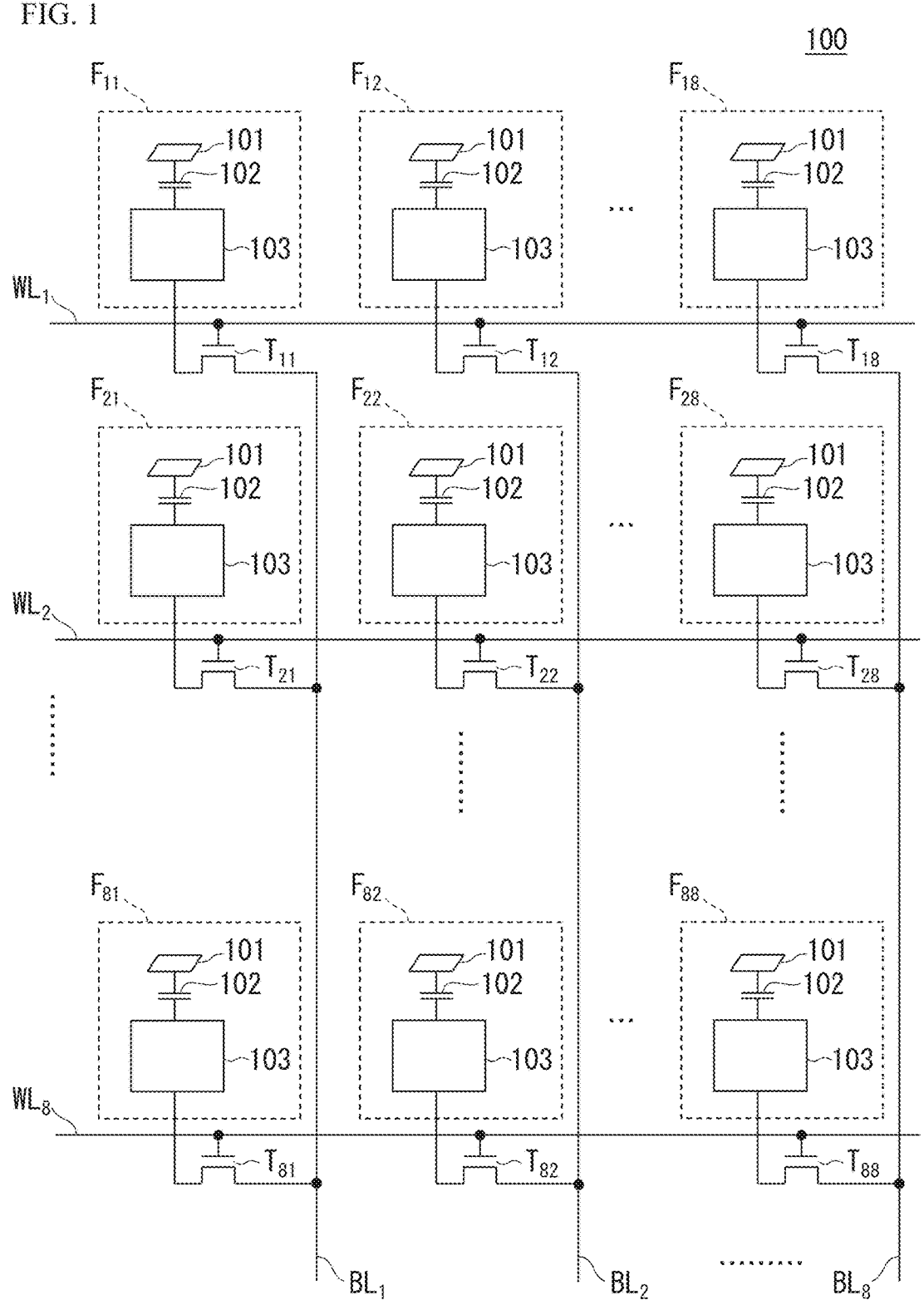
FIG. 1 is a diagram showing an example of a circuit configuration of a signal detection device according to an embodiment of the invention.

FIG. 1 is a diagram showing an example of a circuit configuration of a signal detection device 100 according to an embodiment of the invention. The signal detection device 100 is a signal detection device which detects a signal generated from a subject.

The device is provided with a plurality of signal detectors F11 to F88 (64 detectors) arranged in a matrix of 8 rows by 8 columns, a plurality of transistors T11 to T88 for signal transfer, a plurality of bit lines BL1 to BL8, and a plurality of word lines WL1 to WL8. In this embodiment, an organism is assumed as the subject. However, the signal detection device 100 according to this embodiment can detect a signal using not only an organism but also an arbitrary object as the subject. For example, the signal detection device 100 can detect not only a biosignal but also a signal distribution of a complicated surface of an industrial product such as a circuit board mounted with an electronic component. Accordingly, the object which becomes the subject of the signal detection device 100 according to the invention is arbitrary.

Here, among the signal detectors F11 to F88 arranged in the matrix, output portions of the signal detectors F11 to F81 belonging to the first column are connected to the bit line BL1 via the transistors T11 to T81 for signal transfer, and output portions of the signal detectors F12 to F82 belonging to the second column are connected to the bit line BL2 via the transistors T12 to T82 for signal transfer. Similarly, output portions of the signal detectors F18 to F88 belonging to the eighth column are connected to the bit line BL8 via the transistors T18 to T88 for signal transfer.

In addition, among the signal detectors F11 to F88 arranged in the matrix, gates of the transistors T11 to T18 for signal transfer provided in the signal detectors F11 to F18 belonging to the first row are connected to the word line WL1, and gates of the transistors T21 to T28 for signal transfer provided in the signal detectors F21 to F28 belonging to the second row are connected to the word line WL2. Similarly, gates of the transistors T81 to T88 for signal transfer provided in the signal detectors F81 to F88 belonging to the eighth row are connected to the word line WL8.

In this embodiment, since the 64 signal detectors F11 to F88 are arranged in the matrix and the transistors T11 to T88 for signal transfer are selected by the word lines WL1 to WL8 and the bit lines BL1 to BL8, signals can be selectively read from the respective signal detectors F11 to F88. In the example of FIG. 1, a total of 64 signal detectors F11 to F88 of 8 rows by 8 columns are provided. However, the invention is not limited to this example and the number of the signal detectors is arbitrary. The number of the transistors for signal transfer, the number of the word lines, and the number of the bit lines are also arbitrary in accordance with the number of the signal detectors.

Figure 2:
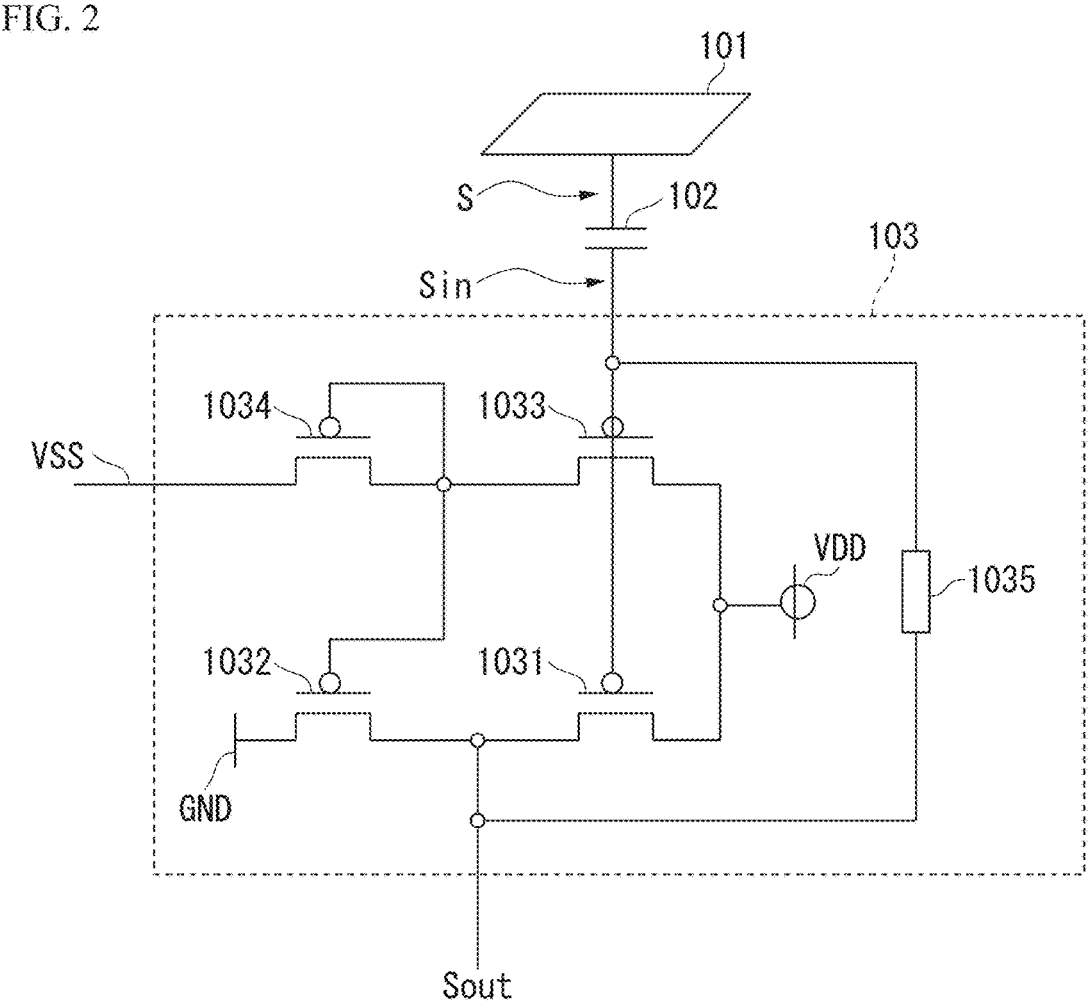
FIG. 2 is a diagram showing an example of a circuit configuration of a signal detector of the signal detection device according to an embodiment of the invention.

FIG. 2 is a diagram showing an example of the circuit configuration of the signal detectors F11 to F88 shown in FIG. 1. All the signal detectors F11 to F88 have the same configuration. As shown in FIG. 2, each of the signal detectors F11 to F88 is provided with an electrode 101, a capacitor 102, and an amplifier 103. The electrode 101 is brought into contact with a subject (not shown), and from this subject, a biosignal (electric signal) is applied to the electrode 101. In this embodiment, the electrode 101 may be made of a gel-like conductive material (conductive gel) in which a carbon nanomaterial doubly covered with molecules constituting a hydrophilic ionic liquid and a water-soluble polymer is dispersed in a water-soluble polymer medium and the water-soluble polymer is crosslinked. In that case, the electrode 101 has excellent flexibility and bendability. Details thereof will be described later.

The capacitor 102 is used to cut a DC component included in the biosignal from the subject, and is connected between the electrode 101 and an input portion of the amplifier 103. That is, the input portion of the amplifier 103 is capacitively coupled to the electrode 101 via the capacitor 102. The capacitor 102 has a capacitance value of approximately 670 nF, and may have an SAM/AlO$_x$ structure formed of a self-assembled monolayer (SAM) and aluminum oxide (AlO$_x$). As will be described later, the capacitor 102 is formed using a thin film and has flexibility.

The amplifier 103 is formed of transistors 1031 to 1034 and a resistance element 1035. In this embodiment, the transistors 1031 to 1034 are p-type organic transistors having flexibility. The organic transistor of the amplifier 103 has a gate width of, for example, 600 μm, and a gate length of 20 μm. In this example, a drain current of approximately −100 μA is confirmed. However, the invention is not limited to this example and an n-type organic transistor may be used in place of the p-type organic transistor. The p-type organic transistor is more advantageous than the n-type organic transistor in consideration of the stability of the operation and a difference in the mobility of the carrier because the p-type organic transistor can stably obtain a larger drain current than the n-type organic transistor. The amplifier 103 is not limited to the organic transistor and can be configured using an arbitrary amplifying element depending on the intended use.

The drain of the transistor 1031 of the amplifier 103 is connected to a power supply node (high-potential node) VDD, and the gate of the transistor 1031 is connected to the input portion of the amplifier 103. The drain of the transistor 1032 is connected to the source of the transistor 1031, and the source of the transistor 1032 is connected to a ground node GND. The drain of the transistor 1033 is connected to the power supply node VDD, and the gate of the transistor 1033 is connected to the input portion of the amplifier 103.

The drain and the gate of the transistor 1034 are connected to the source of the transistor 1033 together with the gate of the transistor 1032, and the source of the transistor 1034 is connected to a low-potential node VSS. The resistance element 1035 is connected between the input portion and the output portion of the amplifier 103. The resistance element 1035 is used to feedback an output signal of the amplifier 103 to the input portion. The resistance element 1035 has a resistance value of approximately 20 MΩ and is made of, for example, a flexible and conductive carbon paste. However, the invention is not limited to this example and the resistance element 1035 can be formed using an arbitrary material. In addition, the resistance element 1035 is not required to be formed integrally with the amplifier 103 and may be provided as an external resistance.

Figure 3A:
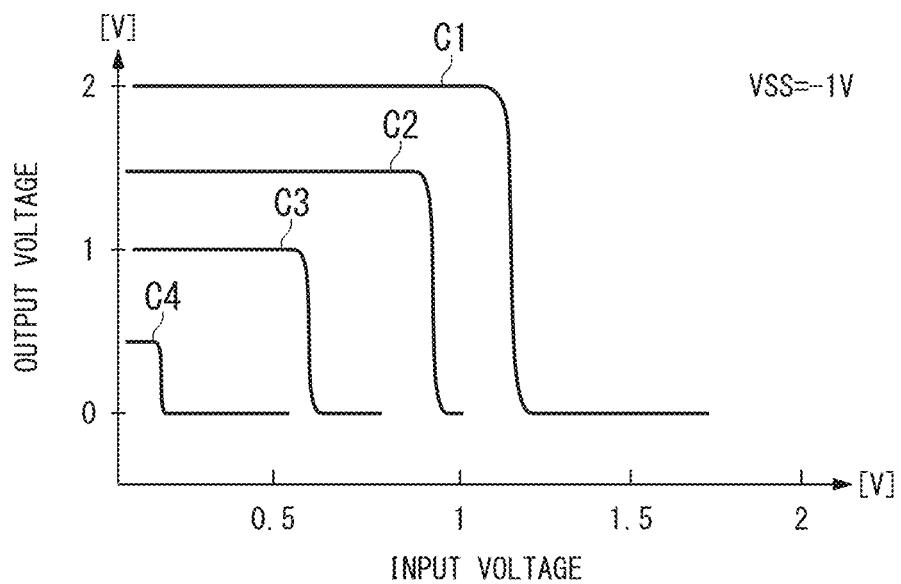
FIG. 3A to 3B show an example of static characteristics of a signal detector of the signal detection device according to an embodiment of the invention.
Figure 3B:
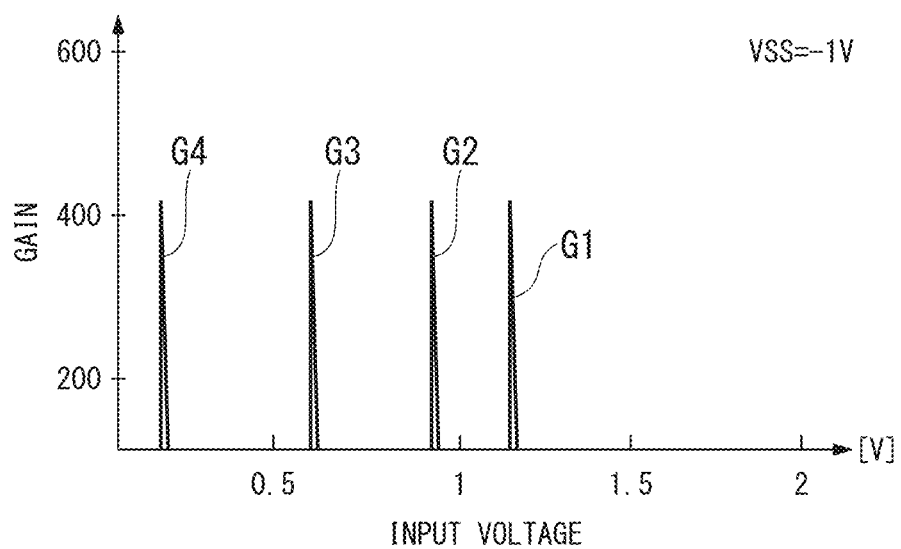

FIG. 3A to 3B schematically show static characteristics of the amplifier 103. FIG. 3A shows an example of input/output characteristics of the amplifier 103, and FIG. 3B shows an example of the relationship between the gain and the input voltage of the amplifier 103. Here, the gain of the amplifier 103 shown in FIG. 3B indicates a change of the output voltage with respect to a change of the input voltage in the input/output characteristics shown in FIG. 3A and is obtained from the inclination of the tangent of the input/output characteristics at each input voltage. In the example of FIGS. 3 A to 3B, a potential of the low-potential node VSS is set to −1 V.

In FIG. 3A, characteristics C1 to C4 indicate the input/output characteristics of the amplifier 103 when the voltage of the power supply node VDD is 2 V, 1.5 V, 1 V, and 0.5 V, respectively. As shown by the characteristics C1 to C4, the amplifier 103 has a transition region where the output voltage is largely changed with a minute change of the input voltage in accordance with the voltage of the power supply node VDD. As shown in FIG. 3B, a large gain is obtained with respect to an input voltage in the transition region. The operation point of the amplifier 103 is set in the transition region.

In FIG. 3B, the characteristics G1 to G4 are gain characteristics of the amplifier 103 when the voltage of the power supply node VDD is 2 V, 1.5 V, 1 V, and 0.5 V, respectively. In the example shown in FIG. 3B, a gain of 400 or greater is obtained even when the voltage of the power supply node VDD is 0.5 V. According to the inventors of the invention, it is confirmed that an input voltage of 1.2 mV is amplified to 220 mV, and 183 is obtained as a gain of the amplifier 103. When the amplifier 103 is operated in such an operation region, a weak biosignal (input voltage) can be effectively amplified. In this embodiment, since the amplifier 103 is operated in the above-described operation region, the operation point of the amplifier 103 can be adjusted by selecting the potential of the low-potential node VSS.

The inventors of the invention have compared the static characteristics of the amplifier 103 before and after attachment to a heart of a rabbit, and confirmed that the static characteristics of the amplifier 103 change little. That is, it is confirmed that the input/output characteristics of the amplifier 103 are rarely influenced by the environment of an organism which is a subject. Accordingly, a biosignal of the subject can be stably amplified.

Figure 4:
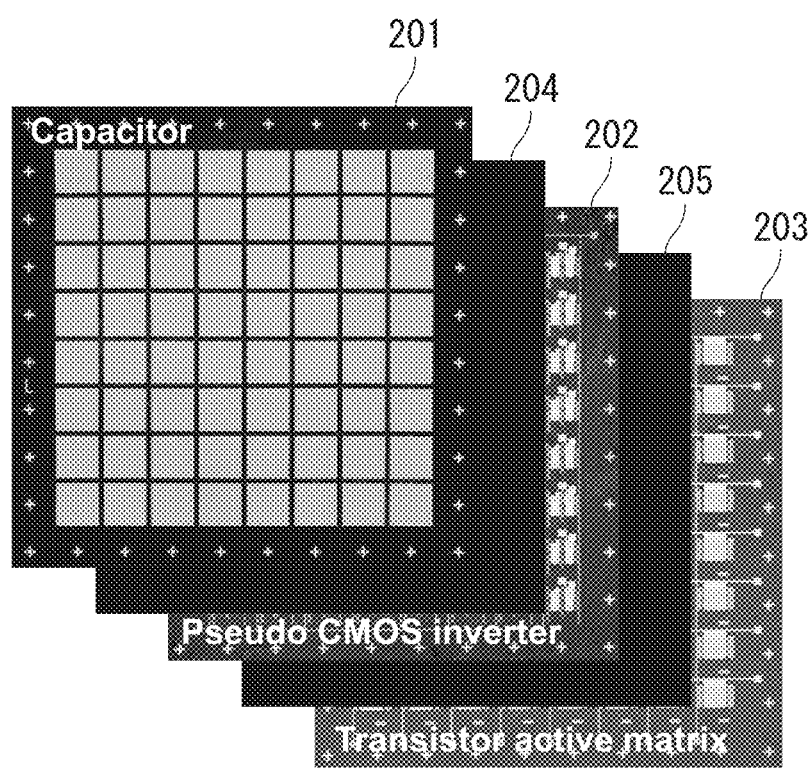
FIG. 4 is a diagram schematically showing a device structure (laminated structure) of the signal detection device according to an embodiment of the invention.
Figure 5:
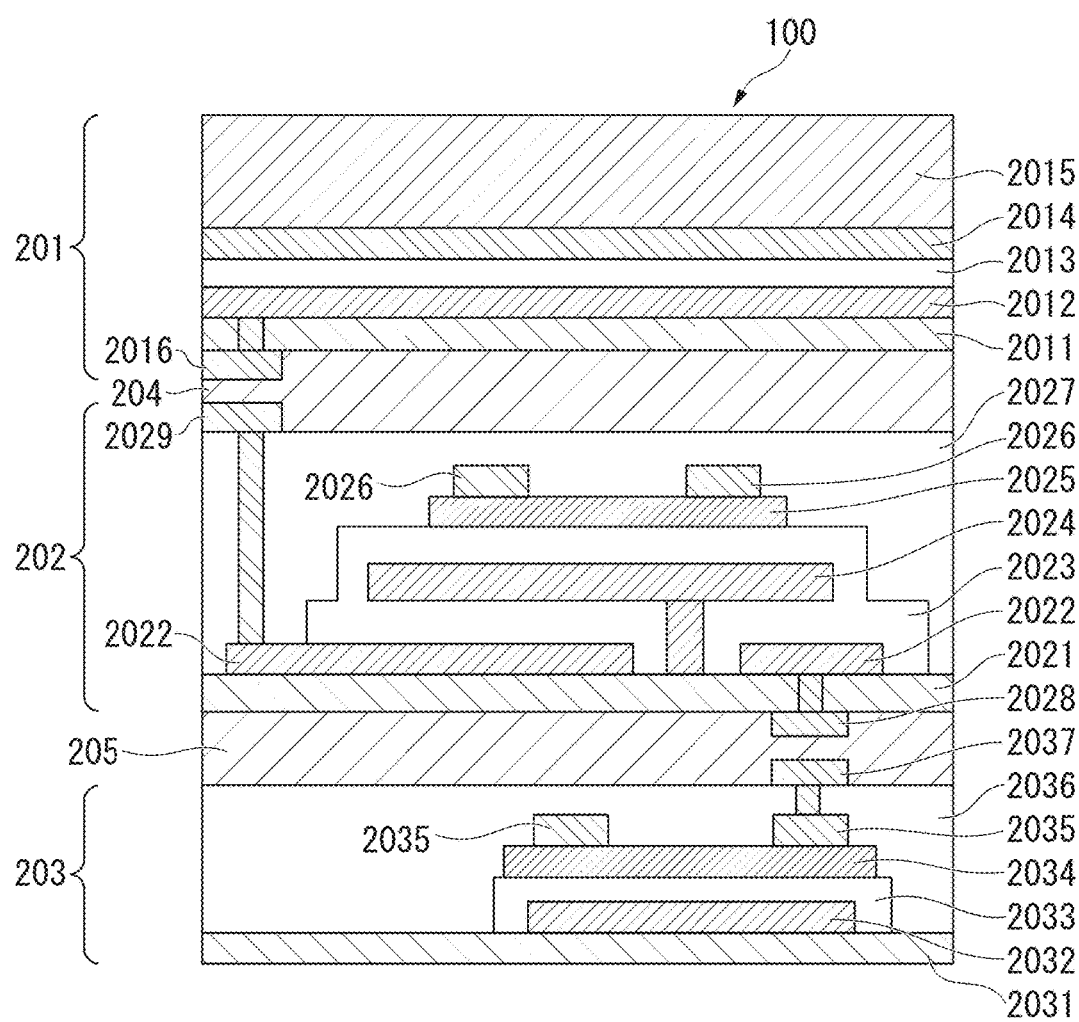
FIG. 5 is a diagram schematically showing a device structure (cross-section structure) of the signal detection device according to an embodiment of the invention.

Next, a device structure of the signal detection device 100 will be described. FIG. 4 is a diagram schematically showing the device structure of the signal detection device 100. As shown in FIG. 4, generally, the signal detection device 100 is formed of an electrode circuit layer (first circuit layer) 201, an amplifier circuit layer (second circuit layer) 202, a transfer circuit layer (third circuit layer) 203, and conductive layers 204 and 205, each formed of an anisotropic conductive sheet, and has a laminated structure in which the electrode circuit layer 201, the amplifier circuit layer 202, and the transfer circuit layer 203 are integrally laminated into roughly a sheet via the conductive layers 204 and 205 as shown in FIG. 5 to be described later. In this embodiment, each of the anisotropic conductive sheets which become the conductive layers 204 and 205 has a thickness of approximately 10 μm. In this embodiment, the anisotropic conductive sheet is made of, for example, a material in which conductive particles are uniformly dispersed in an adhesive having a high insulation property. A member which is used to electrically connect electrodes to each other in an electronic component of a liquid crystal display or the like can be used.

Here, the electrode circuit layer 201 is a circuit layer formed by arranging the electrode 101 and the capacitor 102 shown in FIG. 2 in a matrix corresponding to the signal detectors F11 to F88 shown in FIG. 1. The amplifier circuit layer 202 is a circuit layer formed by arranging the amplifier 103 shown in FIG. 2 in a matrix. The transfer circuit layer 203 is a circuit layer formed by arranging the transistors T11 to T88 for signal transfer shown in FIG. 1 in a matrix. In this embodiment, the word lines WL1 to WL8 and the bit lines BL1 to BL8 are formed in the transfer circuit layer 203. However, the invention is not limited to this example, and the word lines WL1 to WL8 and the bit lines BL1 to BL8 may be formed in any circuit layer.

FIG. 5 is a diagram showing an example of a cross-section structure of the signal detection device 100 having a laminated structure. As shown in FIG. 5, the electrode circuit layer 201, the amplifier circuit layer 202, and the transfer circuit layer 203 are laminated via the conductive layers 204 and 205, each formed of an anisotropic conductive sheet. Each circuit layer will be described in detail. The electrode circuit layer 201 is a circuit layer in which the electrode 101 and the capacitor 102 of FIG. 2 are formed, and is formed of a polyimide layer 2011 (for example, thickness 1.2 μm) which is a flexible base, a metal layer 2012 (for example, Al having a thickness of 30 nm) serving as one electrode of the capacitor 102 shown in FIG. 2, an $AlO_x$/SAM layer 2013 (for example, $AlO_x$ having a thickness of 4 nm+SAM having a thickness of 2 nm) serving as an insulating layer of the capacitor 102, a metal layer 2014 (for example, Au having a thickness of 50 nm) serving as the other electrode of the capacitor 102, a conductive gel layer 2015 serving as the electrode 101 shown in FIG. 2, and a metal layer 2016 (Au) connected to the metal layer 2012. The thickness of the conductive gel layer 2015 is approximately 0.1 mm to 1 mm. The metal layer 2016 is exposed to the lower surface of the electrode circuit layer 201. In this embodiment, the $AlO_x$/SAM layer 2013 which forms the insulating layer of the capacitor 102 is formed so as to seal the amplifier circuit layer 202 on the lower layer side when viewed from the conductive gel layer 2015. That is, in this embodiment, the member constituting the electrode circuit layer 201 forms a sealing layer which seals the amplifier circuit layer 202.

The amplifier circuit layer 202 is a circuit layer in which the amplifier 103 having an input portion capacitively coupled to the electrode 101 of FIG. 2 is formed, and is formed of a polyimide layer 2021 (for example, thickness 1.2 μm) which is a flexible base, a metal layer 2022 (for example, Al having a thickness of 30 nm) serving as wiring, an $AlO_x$/SAM layer 2023 (for example, $AlO_x$ having a thickness of 4 nm+SAM having a thickness of 2 nm) serving as a gate insulating film of the organic transistor, an aluminum layer 2024 (for example, thickness 30 nm) serving as a gate electrode of the organic transistor, an organic semiconductor layer 2025 (for example, thickness 30 nm) serving as a channel forming layer of the organic transistor, a metal layer 2026 (Au) serving as a source/drain electrode of the organic transistor, a parylen layer 2027 (for example, thickness 2 μm), and metal layers 2028 and 2029 (Au) connected to the wiring. The metal layers 2028 and 2029 are exposed to the lower surface and the upper surface of the amplifier circuit layer 202, respectively.

The transfer circuit layer 203 is a circuit layer in which the transistors T11 to T88 for signal transfer of FIG. 1 for reading an output signal of the amplifier 103 of FIG. 2 are formed, and is formed of a polyimide layer 2031 (for example, thickness 1.2 μm) which is a flexible base, an aluminum layer 2032 (for example, thickness 30 nm) serving as a gate electrode of the organic transistor, an $AlO_x$/SAM layer 2033 (for example, $AlO_x$ having a thickness of 4 nm+SAM having a thickness of 2 nm) serving as a gate insulation film of the organic transistor, an organic semiconductor layer 2034 (for example, thickness 30 nm) serving as a channel forming layer of the organic transistor, a metal layer 2035 (Au) serving as a source/drain electrode of the organic transistor, a parylen layer 2036 (for example, thickness 2 μm), and a metal layer 2037 (Au) connected to the source/drain electrode of the organic transistor. The metal layer 2037 is exposed to the upper surface of the transfer circuit layer 203.

The transfer circuit layer 203 and the amplifier circuit layer 202 are laminated via the conductive layer 205, and thus the metal layer 2037 formed on the upper surface of the transfer circuit layer 203 and the metal layer 2028 formed on the lower surface of the amplifier circuit layer 202 are electrically connected to each other. In this embodiment, the metal layers 2037 and 2028 are electrically connected to each other via the conductive layer 205, and thus, for example, the output portions of the signal detectors F11 to F88 shown in FIG. 1 and the input portions (source/drain) of the transistors T11 to T88 for signal transfer are electrically connected to each other.

The amplifier circuit layer 202 and the electrode circuit layer 201 are laminated via the conductive layer 204, and thus the metal layer 2029 formed on the upper surface of the amplifier circuit layer 202 and the metal layer 2016 formed on the lower surface of the electrode circuit layer 201 are electrically connected to each other. In this embodiment, the metal layers 2029 and 2016 are electrically connected to each other via the conductive layer 204, and thus, for example, the input portion of the amplifier 103 of the signal detector shown in FIG. 2 and one electrode of the capacitor 102 are electrically connected to each other.

In the device structure of the signal detection device 100 shown in FIG. 5, the $AlO_x$/SAM layer 2013 is formed as an insulating layer which seals the amplifier circuit layer 202 between the conductive gel layer 2015 (electrode 101) formed in the electrode circuit layer 201 and the amplifier circuit layer 202, and the electrode 101 and the input portion of the amplifier 103 are capacitively coupled to each other via this insulating layer. Specifically, the capacitor 102 of FIG. 2 formed of the metal layer 2012, the $AlO_x$/SAM layer 2013, and the metal layer 2014 are formed between the conductive gel layer 2015 (electrode 101) and the amplifier circuit layer 202, the conductive gel layer 2015 and the amplifier circuit layer 202 are capacitively coupled to each other by the capacitor 102, and the amplifier circuit layer 202 is sealed relative to the conductive gel layer 2015 due to the laminated structure of the metal layer 2014, the $AlO_x$/SAM layer 2013, and the metal layer 2012. Accordingly, the input portion of the amplifier 103 formed in the amplifier circuit layer 202 is electrically (AC) connected to the electrode 101 of FIG. 2 formed in the electrode circuit layer 201, and the amplifier circuit layer 202 and the transfer circuit layer 203 are separated from the conductive gel layer 2015 by the $AlO_x$/SAM layer 2013 with excellent humidity resistance which is formed in the electrode circuit layer 201. Therefore, even when the conductive gel layer 2015 (electrode 101) is brought into contact with a subject, it is possible to detect a biosignal while suppressing intrusion of moisture or the like from the subject to the amplifier circuit layer 202 or the transfer circuit layer 203. Accordingly, a failure or malfunction of an electronic circuit formed of the amplifiers 103 (FIG. 2) of the signal detectors F11 to F88 shown in FIG. 1 which are formed in the amplifier circuit layer 202 and the transistors T11 to T88 for signal transfer shown in FIG. 1 which are formed in the transfer circuit layer 203 can be suppressed, and a biosignal can be stably detected.

In the device structure of the signal detection device 100 shown in FIG. 5, the wiring (not shown) for reading an output signal $S_{out}$ of the amplifier 103 of FIG. 2 formed in the amplifier circuit layer 202 via the transistors T11 to T88 for signal transfer formed in the transfer circuit layer 203 may be drawn to the lower surface side (one side of the transfer circuit layer 203) of the transfer circuit layer 203 opposite the upper surface side (the other side) of the transfer circuit layer 203 on which the amplifier circuit layer 202 is positioned. In this embodiment, the above-described wiring may be drawn to the lower surface side (one side) of the transfer circuit layer 203 in an outer circumferential region of the transfer circuit layer 203. In addition, in this embodiment, all of the wiring may be drawn to the lower surface side of the transfer circuit layer 203. Accordingly, it is possible to prevent the contact between the wiring drawn to the outside from the signal detection device 100 and the subject.

Here, the thickness of the electrode circuit layer 201 is approximately 2 μm, excluding the conductive gel layer 2015.

The thickness of each of the amplifier circuit layer 202 and the transfer circuit layer 203 is approximately 4 μm, including the parylen layer. As described above, each of the conductive layers 204 and 205 has a thickness of approximately 10 μm. Accordingly, when the thickness of the conductive gel layer 2015 is 0.1 mm, the total thickness from the electrode circuit layer 201 to the transfer circuit layer 203 is approximately 130 μm. Accordingly, the signal detection device 100 having the above-described device structure is formed in a sheet having an extremely small thickness as a whole and has high flexibility. In addition, the capacitors formed in the electrode circuit layer 201 and the respective circuit elements such as the transistors formed in the amplifier circuit layer 202 and the transfer circuit layer 203 also have flexibility. The metal layer formed in each circuit layer is a thin film formed using, for example, a CVD method, and has high flexibility. The conductive gel, to be described later, which forms the conductive gel layer 2015 (electrode 101) has extremely excellent biocompatibility and flexibility. The $AlO_x$/SAM layer 2013 which separates the amplifier circuit layer 202 from the conductive gel layer 2015 brought into contact with the subject has excellent humidity resistance. Accordingly, the signal detection device 100 provided by laminating the above-described electrode circuit layer 201, amplifier circuit layer 202, transfer circuit layer 203, and conductive layers 204 and 205 has high flexibility and humidity resistance and characteristics suitable for signal detection in a biological environment. According to the inventors of the invention, a weak Young's modulus of 1 kPa is confirmed as an evaluation value related to the flexibility of the signal detection device 100. Accordingly, the signal detection device 100 according to this embodiment is softer than a brain which is said to have a Young's modulus of 1 kPa to 10 kPa comparable to the food product pudding. Accordingly, for example, the signal detection device 100 can be attached firmly to the sulcus, and thus signals related to the activity in the sulcus, occupying many signals generated from the brain, can also be effectively detected.

In this embodiment, in a state in which the amplifier circuit layer 202 is interposed between the electrode circuit layer 201 and the transfer circuit layer 203, the electrode circuit layer 201, the amplifier circuit layer 202, and the transfer circuit layer 203 are laminated. In addition, in this embodiment, the electrode circuit layer 201 and the transfer circuit layer 203 may have the same bending rigidity. According to the laminated structure, the amplifier circuit layer 202 in which the amplifier 103 is formed is positioned around the neutral axis of bending of the signal detection device 100. Therefore, when the sheet-like signal detection device 100 is mounted on a subject, the influence of the stress generated by bending the signal detection device 100 along the surface shape of the subject can be reduced as much as possible. Accordingly, with respect to the bending of the sheet-like signal detection device 100, the electric characteristics of the amplifier 103 can be stabilized and the signal of the subject can be stably detected.

Although omitted in FIG. 5, in an edge portion of the laminated structure of the signal detection device 100, the amplifier circuit layer 202 is also sealed by the sealing layer formed by the electrode circuit layer 201.

[Description of Operation]

Next, a basic operation of the above-described signal detector shown in FIG. 2 will be described with reference to FIG. 6A to 6D. In this embodiment, a heart of a rabbit is used as a subject and the signal detection device 100 of FIG. 1 provided with the signal detector of FIG. 2 is attached to a surface of the heart of the rabbit. By adjusting the potential of the low-potential node VSS, the operation point of the amplifier 103 of the signal detector of FIG. 2 is set beforehand in an operation region where a desired gain is obtained.

In a state in which the electrode 101 (conductive gel layer 2015) of the signal detection device 100 is brought into contact with the surface tissue of the heart of the rabbit which is a subject, a biosignal (electric signal) S generated from the heart of the rabbit which is a subject is transferred to the electrode 101.

Figure 6A:
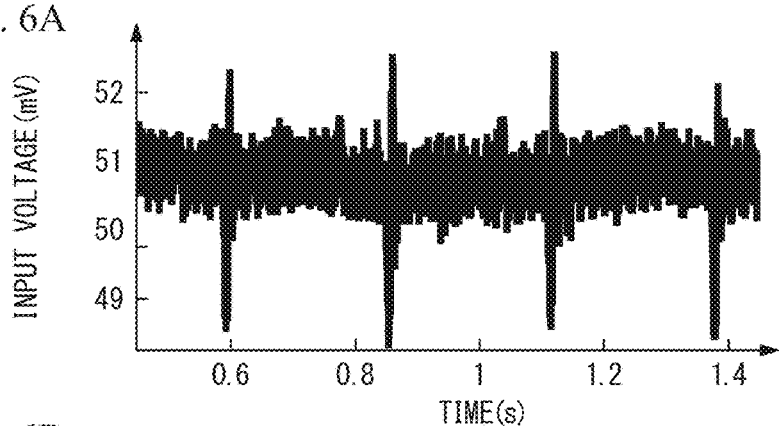
FIG. 6A to 6D show waveform charts for illustrating an operation of the signal detector of the signal detection device according to an embodiment of the invention.

FIG. 6A shows an example of a waveform of the electric signal S generated from the heart of the rabbit which is a subject.

As shown in FIG. 6A, the biosignal S is a pulse signal and is a kind of AC signal. In this example, the pulse amplitude of the biosignal S is approximately 1.2 mV. Since the biosignal S is a kind of AC signal, it is input to the amplifier 103 as an electric signal $S_{in}$ through the capacitor 102. Here, since the electrode 101 and the amplifier 103 are galvanically isolated by the capacitor 102, the potential of the heart of the rabbit does not have an influence on the operation point of the amplifier 103.

The amplifier 103 amplifies the electric signal $S_{in}$ and outputs an output signal $S_{out}$. Specifically, the transistor 1031 is turned on or off in accordance with the signal level of the electric signal $S_{in}$. The inverter formed of the transistors 1033 and 1034 outputs an inversion signal of the electric signal $S_{in}$ to the gate of the transistor 1032. Accordingly, the transistors 1031 and 1032 perform the switching operation in a complementary manner, and the transistors 1031 to 1034 are operated as a pseudo inverter circuit having a complementary metal oxide semiconductor (CMOS) configuration. As a result of this switching operation, a pulsed output signal $S_{out}$ is output from the connection node between the source of the transistor 1031 and the drain of the transistor 1032, that is, the output portion of the amplifier 103. Hereinbelow, the inverter circuit formed of the transistors 1031 to 1034 will be referred to as a pseudo CMOS inverter circuit. The output signal $S_{out}$ of the pseudo CMOS inverter circuit is negatively fed back to the input portion of the amplifier 103 via the resistance element 1035.

Here, if the level of the electric signal $S_{in}$ provided to the input portion of the amplifier 103 is not changed, the signal level of the output signal $S_{out}$ of the amplifier 103 is stable at an operation point determined by the input/output characteristics of the pseudo CMOS inverter circuit formed of the transistors 1031 to 1034 and the resistance value of the resistance element 1035. This operation point is present in the above-described operation region where the gain is increased, that is, the operation region where the change of the output signal is increased with respect to the change of the input signal.

When the pulse of the electric signal $S_{in}$ supplied from the electrode 101 via the capacitor 102 is generated in a state in which the amplifier 103 is stable at the above-described operation point, the signal level of the output signal $S_{out}$ of the amplifier 103 is changed in response to the signal level of the pulse. At this time, since the amplifier 103 is operated in the operation region where a large gain is obtained, the signal level of the electric signal $S_{in}$ is amplified and a large signal level is obtained as the output signal $S_{out}$. Accordingly, the amplifier 103 amplifies the electric signal $S_{in}$ and outputs the output signal $S_{out}$.

Figure 6B:
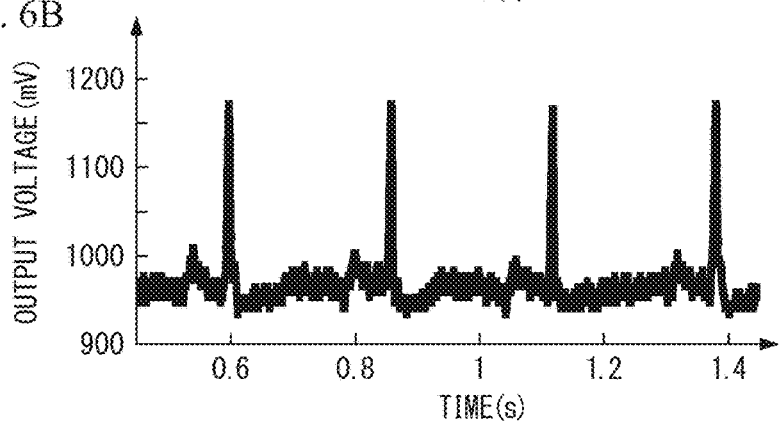

FIG. 6B shows an example of a waveform of the output signal $S_{out}$. In this example, the pulse amplitude of the output signal $S_{out}$ is approximately 220 mV, and 1.2 mV, which is the pulse amplitude of the electric signal $S_{in}$ input to the amplifier 103, is amplified approximately 183-fold. In the example shown in FIG. 6B, the pulse signal on the minus side is not output. A cause for this is thought to be, for example, a failure in adjustment of the operation point. However, such a phenomenon can be solved by measures such as re-adjustment of the operation point and optimized design for the amplifier 103, and this is not an essential problem of the invention.

Figure 6C:
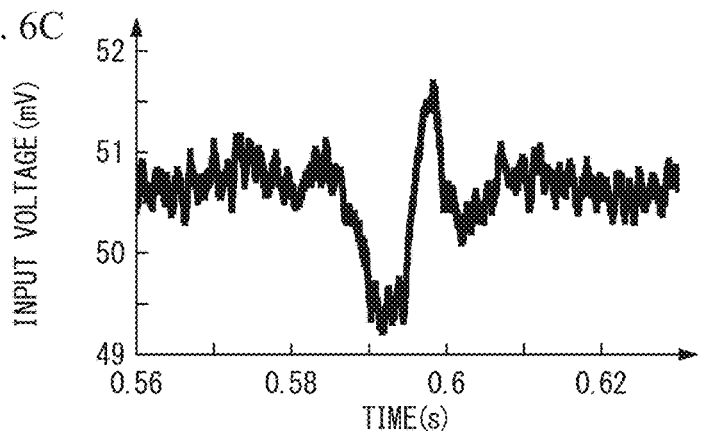
Figure 6D:
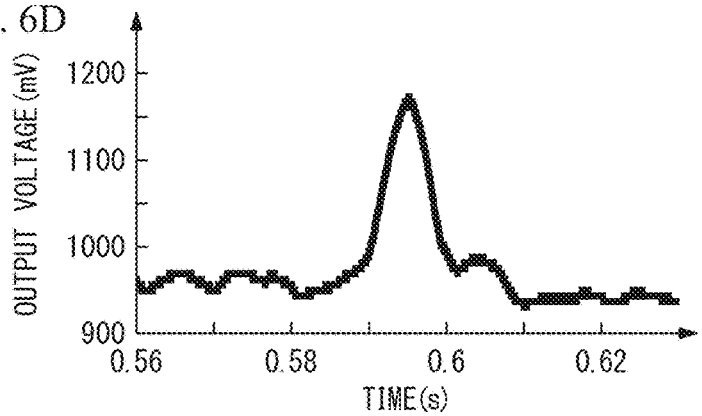

FIG. 6C shows an example of a waveform of the electric signal $S_{in}$ when the heart of the rabbit which is a subject is put in an ischemia state, and FIG. 6D shows an example of a waveform of the output signal $S_{out}$ when the heart of the rabbit which is a subject is put in an ischemia state. From the difference between the signal waveforms shown in FIGS. 6C and 6D, the operator can grasp whether the heart of the rabbit which is a subject is in an ischemia state.

Figure 7A:
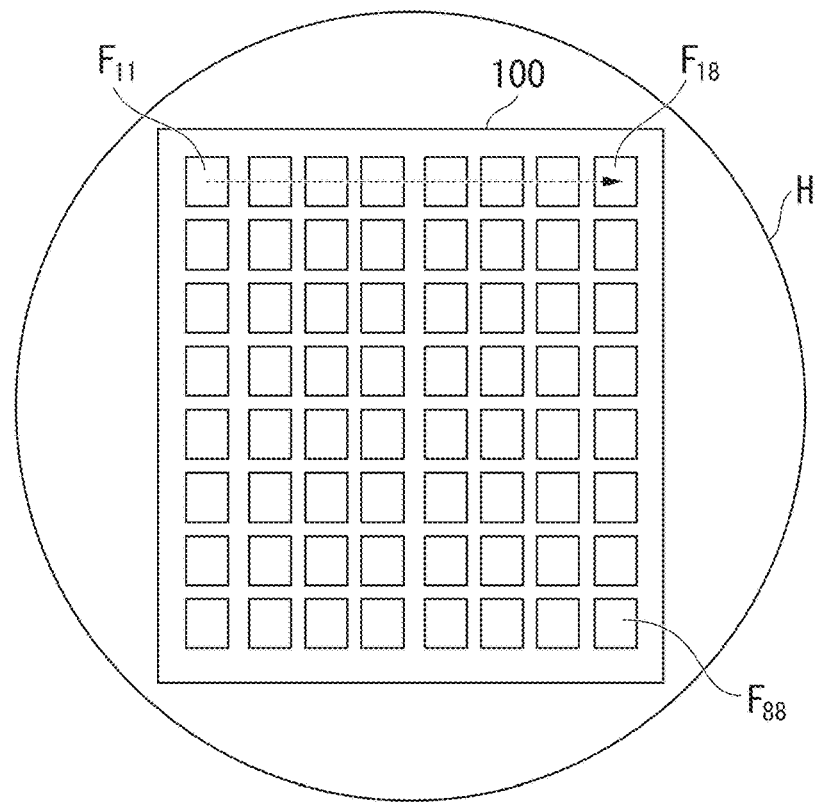
FIG. 7A to 7B show diagrams for illustrating an operation of the signal detection device according to an embodiment of the invention.
Figure 7B:
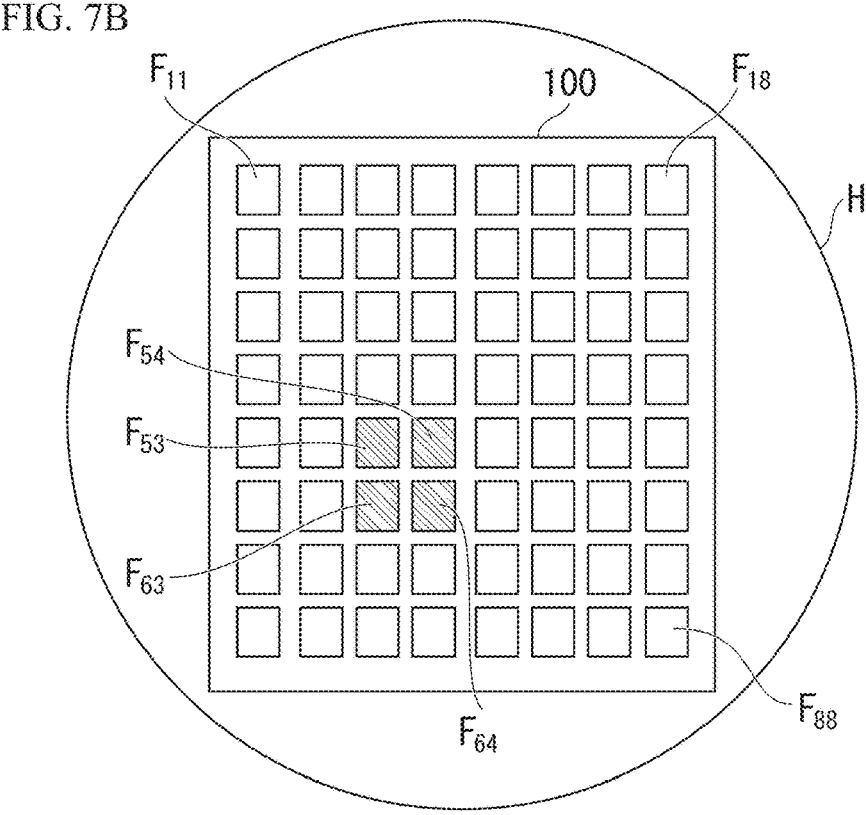

Next, an example of an operation of the signal detection device 100 shown in FIG. 1 will be described with reference to FIG. 7A to 7B. FIG. 7A to 7B schematically show the signal detection device 100 mounted on a heart H of a subject. Although not shown in detail in FIG. 7A to 7B, the signal detection device 100 is mounted on the subject by firmly attaching the conductive gel layer 2015 of the electrode circuit layer 201 to a surface tissue of the heart H of the subject. At this time, since the signal detection device 100 has extremely high flexibility, the conductive gel layer 2015 of the electrode circuit layer 201 of the signal detection device 100 is firmly attached to the surface tissue of the heart H along the surface shape of the heart H without inhibiting the movement of the heart H. Accordingly, a biosignal of the surface tissue of the heart H can be accurately detected.

Next, an example of the operation of this embodiment will be described.

In a state in which the signal detection device 100 is mounted on the heart H of the subject as described above, the word lines WL1 to WL8 are selected using an external information processing device (for example, personal computer) (not shown) to scan and sequentially read output signals of the signal detectors F11 to F88 via the transistors T11 to T88. For example, as shown in FIG. 7A, when the transistors T11 to T18 for signal transfer connected to the signal detectors F11 to F18 of the first row are selected by the word line WL1, output signals $S_{out}$ of the signal detectors F11 to F88 are output to the bit lines BL1 to BL8 via the transistors T11 to T18 for signal transfer, respectively. The signals output to the bit lines BL1 to BL8 are read by the external information processing device. Accordingly, the signal detectors F11 to F18 of the first row are scanned. The scanning is similarly performed also in other rows.

In this example, the word lines WL1 to WL8 and the bit lines BL1 to BL8 of the signal detection device 100 are connected to the external information processing device via an appropriate interface. However, a decoder for selecting the word lines WL1 to WL8 and a selector (multiplexor) for selecting the bit lines BL1 to BL8 may be provided in an arbitrary one of the electrode circuit layer 201, the amplifier circuit layer 202, and the transfer circuit layer 203. In this case, the signal detectors F11 to F88 are sequentially scanned via the decoder and the selector. For example, as shown in FIG. 7A, in a state in which the signal detectors F11 to F18 of the first row at the forefront are selected by the word line WL1 of FIG. 1, signals output to the bit lines BL1 to BL8 from the signal detectors F11 to F88 are sequentially selected by the selector.

The signals (output signals of the signal detectors) of the bit lines sequentially read as described above are input to an external information processing device (not shown). This external information processing device generates a strength distribution of the output signals of the signal detectors (amplifiers) by performing a predetermined signal process on the input signals. For example, the external information processing device converts the output signals of the signal detectors into digital signals through sampling, generates a strength distribution (two-dimensional signal strength distribution) of the output signals of the signal detectors F11 to F18 of the first row, and displays it on a display portion (not shown). Similarly, the scanning is performed on the signal detectors of another row and a strength distribution of the output signals of all the signal detectors F11 to F88 is obtained. The operator can specify a part where a signal strength indicating abnormality is generated from the strength distribution obtained through the above-described scanning. However, the invention is not limited to this example and the display form of the signal strength is arbitrary.

FIG. 7B shows an example of the positions of the signal detectors in which an abnormal signal strength is detected.

In this example, the signal detectors F53, F54, F63, and F64 correspond to the signal detectors in which an abnormal signal strength is detected. In this case, the operator analyzes the strength distribution of the signals, specifies an abnormal part, and inputs an instruction for reading the output signals of the signal detectors F53, F54, F63, and F64 arranged in the abnormal part to the external information processing device. Based on the instruction (result of the analysis of the strength distribution of the signals), the external information processing device monitors a biosignal of the abnormal part of the subject with time by simultaneously reading the output signals of the signal detectors F53, F54, F63, and F64 arranged in the abnormal part. The external information processing device displays, on a display portion, the biosignal obtained by monitoring as a waveform, a graph, a numerical value, or the like.

In this case, the signals detected by the signal detectors F53, F54, F63, and F64 may be synthesized (combined) into one signal and input to the external information processing device, or may be separately input. Regarding the part where an abnormal signal strength is shown, when the number of the signal detectors to be selected by the above-described decoder and selector is increased, the quantity of the information included in the signals is increased, and thus the biosignal can be accurately monitored.

According to the device structure of the signal detection device 100 shown in FIG. 5 according to the above-described embodiment, since the electrode 101, the capacitor 102, and the amplifier 103 shown in FIG. 2 are configured integrally with each other, the transfer route of the signal from the electrode 101 to the amplifier 103 can be reduced. Accordingly, the influence of the noise in the transfer route of the signal from the electrode 101 to the input portion of the amplifier 103 can be suppressed, and the signal to noise ratio of the detection signal can be improved. Therefore, even when the intervals between the signal detectors F11 to F88 are small, the biosignal can be detected. Accordingly, the signal detectors F11 to F88 can be densely arranged and the strength distribution of the biosignal can be accurately acquired.

According to the device structure of the signal detection device 100 shown in FIG. 5 according to this embodiment, the transistors of the amplifier circuit layer 202 and the transfer circuit layer 203 are sealed when viewed from the conductive gel layer 2015 of the electrode 101 of FIG. 2. Accordingly, even when the electrode 101, the capacitor 102, and the amplifier 103 are formed integrally with each other and the signal detection device 100 is attached to an organism which is a subject over a long period of time, moisture or the like intruding into the amplifier 103 from the organism can be suppressed. Accordingly, a failure or malfunction of the amplifier 103 can be suppressed and reliability of the signal detection can be maintained.

According to the device structure of the signal detection device 100 shown in FIG. 5 according to this embodiment, excellent flexibility can be obtained. Accordingly, even when the signal detection device 100 is attached to a subject, the electrode 101 can be firmly attached to a surface of a tissue of the subject without inhibiting the movement of the subject. Accordingly, a biosignal generated from the subject can be accurately and stably detected.

According to the circuit configuration of the signal detection device 100 shown in FIG. 1 according to this embodiment, the plurality of signal detectors F 11 to F88 can be arbitrarily selected. Accordingly, when the signal detection device 100 is mounted on a subject, there is no need to strictly specify beforehand a monitoring part to mount the signal detection device 100 on the subject. Accordingly, the signal detection device 100 can be easily mounted on the subject.

According to the circuit configuration of the signal detection device 100 shown in FIG. 1 according to this embodiment, the plurality of signal detectors F11 to F88 can be arbitrarily selected. Accordingly, it is possible to easily specify not only an abnormal part but also a target part to monitor a biosignal, and a biosignal of an arbitrary part can be selectively detected within the range in which the signal detectors F11 to F88 are positioned.

[Conductive Gel]

Next, the conductive gel which forms the electrode 101 (conductive gel layer 2015) will be described.

The conductive gel which forms the electrode 101 according to an embodiment of the invention includes a carbon nanomaterial. This carbon nanomaterial is doubly covered with molecules constituting a hydrophilic ionic liquid and a water-soluble polymer.

When conductive paper is produced by, for example, making the double-covered carbon nanomaterial into paper, contact with this conductive paper is possible without direct contact with the carbon nanomaterial itself. Similarly, when the double-covered carbon nanomaterial is mixed with a material of an object other than paper and the object is produced, contact with the object is possible without direct contact with the carbon nanomaterial itself.

In the composition of the conductive gel which forms the electrode 101 according to an embodiment of the invention, a carbon nanomaterial covered with molecules constituting a hydrophilic ionic liquid is dispersed in a water-soluble polymer medium, and the carbon nanomaterial is doubly covered with the molecules of the ionic liquid and the water-soluble polymer.

It is preferable that the carbon nanomaterial be covered with a monomolecular film of molecules of the ionic liquid.

The conductive material which is the conductive gel which forms the electrode 101 according to an embodiment of the invention is a material in which a carbon nanomaterial doubly covered with molecules constituting a hydrophilic ionic liquid and a water-soluble polymer is dispersed in a water-soluble polymer medium and the water-soluble polymer is crosslinked.

In this specification, the ionic liquid is salt in a molten state in a wide temperature range including room temperature, called normal temperature molten salt, or simply molten salt.

As the hydrophilic ionic liquid, hydrophilic ionic liquids can be used among various known ionic liquids. Examples thereof include N,N-diethyl-N-methyl-N-(2-methoxyethyl) ammonium tetrafluoroborate (DEMEBF$_4$).

In this specification, the carbon nanomaterial is a material in which constituent elements (for example, one CNT) composed of carbon atoms and structured to have a nanometer size are elements with carbon atoms bonded to each other with a van der Waals force, e.g., carbon nanotubes, carbon nanofibers (fibers having a diameter of 10 nm or less among carbon fibers), carbon nanohorns, or fullerenes. Superior dispersibility is exhibited in water when a fine carbon nanomaterial having a diameter of 10 nm or less is used.

Carbon nanomaterials of the same kind or a plurality of kinds may be used.

The carbon nanotubes have a structure in which a graphene sheet with carbon atoms arranged in a hexagonal net-like pattern is cylindrically rounded in a single layer or in multiple layers (called single-walled nanotube (SWNT), double-walled nanotube (DWNT), and multi-walled nanotube (MWNT)). The carbon nanotubes which can be used as the carbon nanomaterial are not particularly limited and may be any of SWNTs, DWNTs, and MWNTs. In general, the carbon nanotubes can be manufactured through a laser ablation method, arc discharge, a thermal CVD method, a plasma CVD method, a gas phase method, a combustion method, or the like, but carbon nanotubes manufactured by any other methods may be used. A plurality of kinds of carbon nanotubes may be used.

The carbon nanotubes easily aggregate by the van der Waals force therebetween, and thus usually, a plurality of carbon nanotubes forms bundles or aggregates. However, under the presence of an ionic liquid, the bundles or the aggregates can be fragmented by applying a shearing force thereto (the level of the entanglement of the carbon nanotubes is reduced). By sufficient fragmentation, the van der Waals force aggregating the carbon nanotubes can be weakened and the carbon nanotubes can be separated from each other. In addition, the ionic liquid can be adsorbed to the separate carbon nanotubes. As a result, it is possible to obtain a composition formed of carbon nanotubes and an ionic liquid, including carbon nanotube simple substances covered with molecules of the ionic liquid.

Means for applying a shearing force used in the fragmentation process is not particularly limited. A wet pulverization device such as a ball mill, a roller mill, or a vibration mill which can apply a shearing force can be used.

It is thought that by mixing carbon nanotubes and an ionic liquid and performing the fragmentation process, molecules of the ionic liquid bonded to surfaces of the carbon nanotubes having a reduced entanglement level through a "cation-$\pi$" interaction bind the carbon nanotubes through an ionic bond, and thus a gel-like composition is obtained (PTL 2). As will be described later, a single layer of molecules of the ionic liquid can be formed on the surfaces of the carbon nanotubes by rinsing the gel-like composition with, for example, a saline solution or ethanol. Furthermore, a composition in which carbon nanotubes covered with molecules constituting an ionic liquid are dispersed in a water-soluble polymer medium can be produced by mixing the carbon nanotubes covered with the molecules of the ionic liquid with water and a water-soluble polymer.

In this specification, the water-soluble polymer (medium) is not particularly limited as long as it is a polymer which can be dissolved or dispersed in water. The water-soluble polymer can be preferably crosslinked in water. For example, the following examples are included.

1. Synthetic Polymer
 (1) Ionic Polymer
 Polymacrylic Acid (anionic)
 Polystyrene Sulfonic Acid (anionic)
 Polyethyleneimine (cationic)
 MPC Polymer (ampholyte ion)
 (2) Non-ionic Polymer
 Polyvinylpyrrolidone (PVP)
 Polyvinyl Alcohol (polyvinyl acetate saponified product)
 Polyacrylamide (PAM)
 Polyethylene Oxide (PEO)
2. Natural Polymer (mostly polysaccharide)
 Starch
 Gelatin
 Hyaluronic Acid
 Alginic Acid
 Dextran
 Protein (for example, water-soluble collagen)
3. Semisynthetic Polymer (for example, solubilized cellulose)
 Cellulose Derivatives such as
 Carboxymethylcellulose (CMC),
 Hydroxypropylcellulose (HPC), and
 Methylcellulose (MC)
 Water-soluble Chitosan (which can also be classified as "2. Natural Polymer")

For example, polyrotaxane can be exemplified as a specific compound of the water-soluble polymer. Polyrotaxane is formed by arranging blocking groups at both terminals of pseudo polyrotaxane (both terminals of linear molecules) in which openings of cyclic molecules (rotator) are clathrate in a skewered state with linear molecules (axis) so that the cyclic molecules do not leave. For example, polyrotaxane using $\alpha$-cyclodextrin as the cyclic molecules and using polyethylene glycol as the linear molecules can be used.

It is preferable that the water-soluble polymer medium be a compound having a group reacting with a crosslinking agent because a hard film is formed by crosslinking. It is preferable that the water-soluble polymer be photo-crosslinkable to form a fine pattern using the composition or the conductive material of the invention.

The layer of the molecules of the ionic liquid covering the carbon nanomaterial may be a monomolecular layer. The surface of the carbon nanomaterial and the molecules of the ionic liquid are bonded to each other through a "cation-$\pi$" interaction. Therefore, by selecting a combination between the carbon nanomaterial and the ionic liquid in which the bond between the molecules of the ionic liquid is smaller than the bond by the "cation-$\pi$" interaction, the layer of the molecules of the ionic liquid covering the carbon nanomaterial can be formed as a monomolecular layer.

For example, by selecting carbon nanotubes as the carbon nanomaterial and selecting N,N-diethyl-N-methyl-N-(2-methoxyethyl)ammonium tetrafluoroborate (DEMEBF$_4$) as the ionic liquid, the layer of the molecules of the DEMEBF$_4$ covering the carbon nanotubes can be formed as a monomolecular layer. When selecting, for example, polyrotaxane as a water-soluble polymer, a thin polyrotaxane layer having a thickness of approximately 5 nm can be formed on the monomolecular layer of DEMEBF$_4$. In the composition obtained as described above, the carbon nanotubes can be formed to have a high dispersion density, and thus it can be formed as a material having a high conductive property. In a conductive member such as an electrode produced with the conductive material, electrons move and a current thus flows between the carbon nanotubes via the thin DEMEBF$_4$ molecular layer and the polyrotaxane layer.

In the composition or the conductive material of the invention, since the surface of the carbon nanomaterial and the molecules of the ionic liquid are strongly bonded to each other through a "cation-$\pi$" interaction, the molecules of the ionic liquid bonded to the surface of the carbon nanomaterial do not come out of the water-soluble polymer medium. The molecules of the ionic liquid which are not bonded to the surface of the carbon nanomaterial can be removed by rinsing with, for example, a saline solution or ethanol.

According to the composition or the conductive material according to an embodiment of the invention, since the carbon nanomaterial contained therein is doubly covered with molecules of the ionic liquid and the water-soluble polymer, the carbon nanomaterial is not substantially brought into contact with cells in an organism even when being applied to the organism. Since the composition or the conductive material has high bendability, it is excellent in followability with respect to the surface of an organ or the like in an organism, and thus an extremely superior interface can be formed between the composition or the conductive material and the organ or the like. Furthermore, the composition or the conductive material can be formed to have a high conductivity.

The method of manufacturing a conductive material according to an embodiment of the invention includes a first process of mixing a hydrophilic ionic liquid, a carbon nanomaterial, and water to obtain a first dispersion system in which the carbon nanomaterial covered with molecules of the ionic liquid is dispersed, and a second process of mixing the first dispersion system, a water-soluble polymer, and water to obtain a second dispersion system in which the carbon nanomaterial covered with the molecules of the ionic liquid and the water-soluble polymer are dispersed.

In the first process, fragmentation may be performed by applying a shearing force to the carbon nanomaterial.

Accordingly, the carbon nanomaterial can be covered with the hydrophilic ionic liquid in a state in which bundles or aggregates of the carbon nanomaterial are further released.

After the second process, a process of crosslinking the water-soluble polymer to produce a composition in which the carbon nanomaterial is dispersed in the water-soluble polymer medium and the water-soluble polymer thereof is crosslinked may be further provided. Accordingly, formability and workability are improved.

A rinsing process may be further provided to remove molecules of the ionic liquid, which are not bonded to the carbon nanomaterial. Accordingly, formability and workability are improved.

The rinsing process can be performed with a saline solution, ethanol, or a liquid which does not destroy the gel. The rinsing process may be performed in any process.

The composition or the conductive material of the invention may include other substances in such a range so as not to impair the effects of the invention. The method of manufacturing the conductive material of the invention may include other processes in such a range as not to impair the effects of the invention.

Hereinafter, the invention will be described in detail based on examples. These examples are merely examples disclosed to contribute to easily understand the invention, and the invention is not limited to these examples.

EXAMPLES

Figure 8A:
FIG. 8A to 8C show a composition or a conductive material of the invention.

FIG. 8A is a photograph showing a state before ultraviolet (UV) curing of a composition in which carbon nanotubes covered with molecules of N,N-diethyl-N-methyl-N-(2-methoxyethyl)ammonium tetrafluoroborate ($DEMEBF_4$) are dispersed in polyrotaxane. It is found that the obtained composition is in a gel-like state (in this specification, "gel-like state" means a state of losing fluidity or a state of substantially losing fluidity, compared to a liquid state having fluidity).

To produce this composition, 30 mg of commercially available carbon nanotubes (MWNT, length: 10 μm, diameter: 5 nm) and 60 mg of N,N-diethyl-N-methyl-N-(2-methoxyethyl)ammonium tetrafluoroborate ($DEMEBF_4$) as a hydrophilic ionic liquid were mixed and stirred in deionized water at 25° C. for a week using a magnetic stirrer at 700 rpm or higher. The obtained suspension was processed using a high-pressure jet milling homogenizer (60 MPa; Nano-jetpal, JN10, Jokoh) to obtain a black substance. The obtained CNT gel-containing solution was rinsed with a saline solution, and then mixed with 1 mg of a photo-crosslinking agent (Irgacure 2959, manufactured by Nagase & Co., Ltd.) and 1000 mg of a polyrotaxane gel ("photo-crosslinkable slide-ring gel", manufactured by Advanced Softmaterials Inc.) to produce the above-described composition.

Figure 8B:
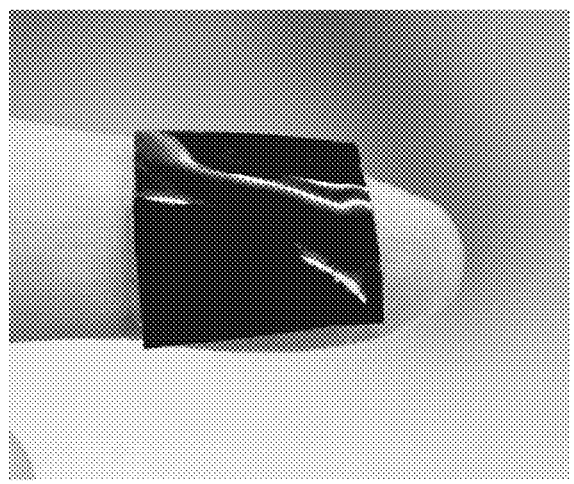

FIG. 8B is a photograph of a sheet obtained by curing the composition shown in FIG. 8A by ultraviolet irradiation (wavelength: 365 nm) for 5 minutes.

The Young's modulus of the obtained sheet was lower than 10 kPa. The Young's modulus of silicon is approximately 100 GPa and the Young's modulus of a conventional plastic film is 1 GPa to 5 GPa. Accordingly, it is found that the obtained sheet is extremely soft. In addition, the Young's modulus of a brain is 1 kPa to 2 kPa and the Young's modulus of muscle cells of a heart is approximately 100 kPa. Accordingly, it was found that the composition or the conductive material of an embodiment of the invention is the same as or higher than an organ in softness. Therefore, an extremely superior interface having high followability with respect to the surface of an organ can be formed between the composition or the conductive material and the organ.

Figure 8C:
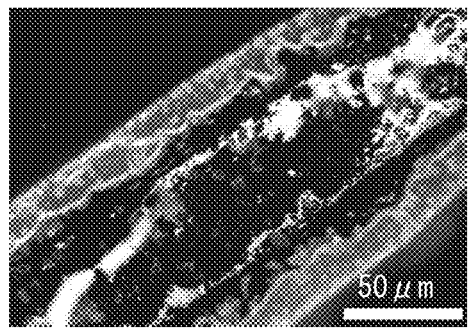

FIG. 8C is an optical microscope photograph of the material, subjected to photo-crosslinking and patterning of a microstructure having a line width of approximately 50 μm using an ultrafine digital UV exposure system ("digital exposure device", manufactured by PMT Corporation). As described above, the composition or the conductive material of an embodiment of the invention is a micromachinable material.

Since crosslinking can be performed at various wavelengths by changing the kind of the photo-crosslinking material, the means for crosslinking is not limited to UV.

Figure 9A:
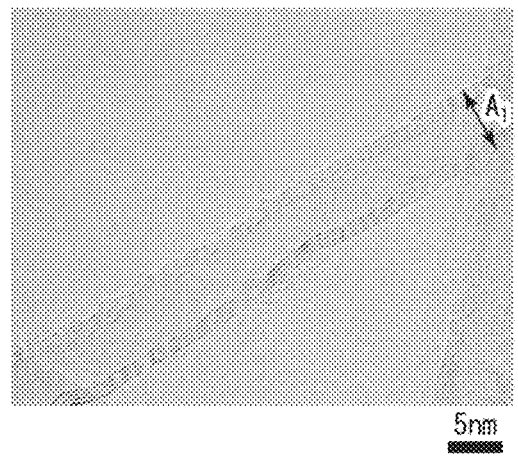
FIG. 9A to 9C show high-resolution cross-sectional transmission electron microscopic images (TEM images).
Figure 9B:
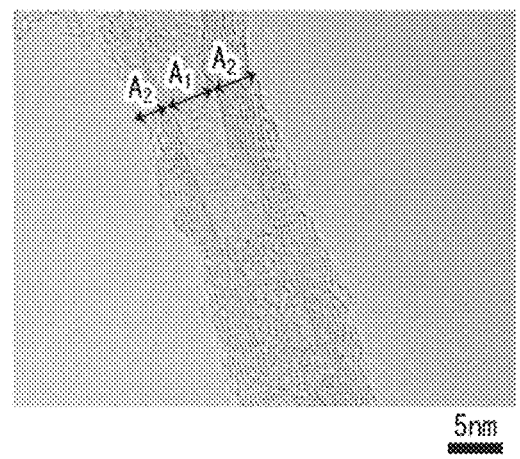
Figure 9C:
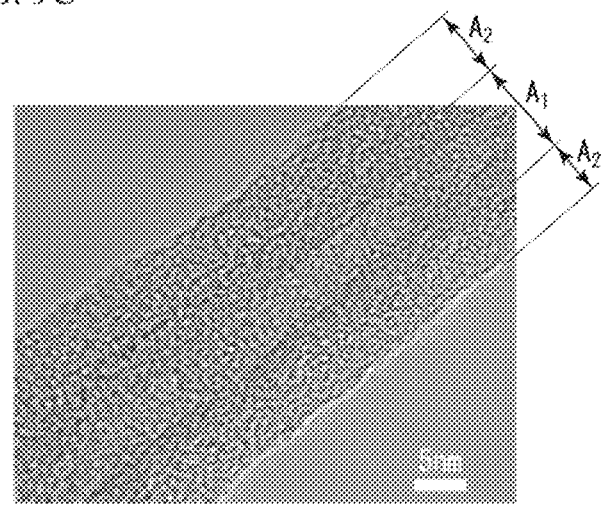

FIG. 9A to 9C show high-resolution cross-sectional transmission electron microscopic images (TEM images). FIG. 9A is a TEM image of carbon nanotubes (MWNT, length: 10 μm, diameter: 5 nm) which can be used in the invention, FIG. 9B is a TEM image of carbon nanotubes covered with polyrotaxane, obtained by mixing 30 mg of carbon nanotubes (MWNT, length: 10 μm, diameter: 5 nm) and 100 mg of polyrotaxane ("photo-crosslinkable slide-ring gel", manufactured by Advanced Softmaterials Inc.) in water without an ionic liquid and performing fragmentation and stirring with a jet mill, and FIG. 9C is a TEM image of a composition obtained under the same conditions as the conditions for producing the composition shown in FIG. 8A.

The HF-2000 Cold-FE TEM (80 kV, manufactured by Hitachi High-Technologies Corporation) was used as the high-resolution cross-sectional transmission electron microscope.

As shown in FIG. 9A, it is found that the used carbon nanotubes $A_1$ are formed of three or four layers.

As shown in FIG. 9B, it is found that the polyrotaxane $A_2$ covers a single carbon nanotube $A_1$, but the cover layer has a nonuniform thickness. In contrast, as shown in FIG. 9C, it is found that the thickness of the polyrotaxane layer $A_2$ covering a single carbon nanotube $A_1$ is extremely uniform and is definitely different from that shown in FIG. 9B.

The difference in thickness uniformity between the cover layers shows that the latter is not a layer in which the molecules of the hydrophilic ionic liquid $DEMEBF_4$ covering the carbon nanotubes are peeled, and the polyrotaxane directly covers the carbon nanotubes, but is a layer in which the polyrotaxane covers the layer of the molecules of the hydrophilic ionic liquid $DEMEBF_4$ covering the carbon nanotubes. If the molecules of the hydrophilic ionic liquid $DEMEBF_4$ covering the carbon nanotubes are peeled and the polyrotaxane covers the carbon nanotubes, the thickness of the cover layer should also be nonuniform in FIG. 9C, similarly to FIG. 9B. In addition, since the carbon nanotubes and the molecules of the $DEMEBF_4$ are bonded to each other with a high cation-π interaction comparable to the hydrogen bond, it is thought that the molecules of the hydrophilic ionic liquid $DEMEBF_4$ covering the carbon nanotubes are not peeled in the above-described processes.

As shown in FIG. 9A to 9C, according to the method of manufacturing a conductive material of the invention, the surface of carbon nanotubes can be uniformly covered with a biocompatible material via molecules of an ionic liquid.

Figure 10:
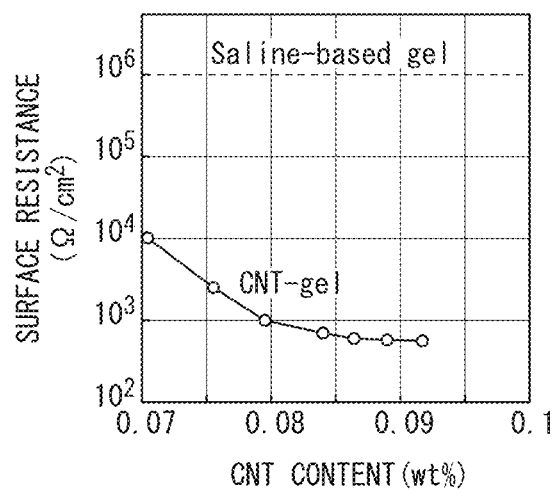
FIG. 10 is a graph showing a surface resistance of the composition (or conductive material) of the invention and carbon nanotube content dependency thereof.

FIG. 10 is a graph showing a surface resistance of the composition (CNT-gel) which is an embodiment of the invention and carbon nanotube content dependency thereof. For comparison, the surface resistance of a gel (saline-based gel) containing a saline solution as a main component is also indicated by the dotted line.

The composition (CNT-gel) is a composition obtained under the same conditions as the conditions for producing the composition shown in FIG. 8A. It has a size of 1 cm by 1 cm and a thickness of 1 mm.

The gel (saline-based gel) containing a saline solution as a main component was obtained by mixing 1 mg of a photo-crosslinking agent with 300 mg of a rotaxane gel, dissolving the mixture with 100 ml of a saline solution, and then performing photo-crosslinking by UV. It has a size of 1 cm by 1 cm and a thickness of 1 mm.

As shown in FIG. 10, it was found that the surface resistance of the composition which is an embodiment of the invention is at least two to three orders of magnitude lower than a conventional gel containing a saline solution as a main component.

Figure 11:
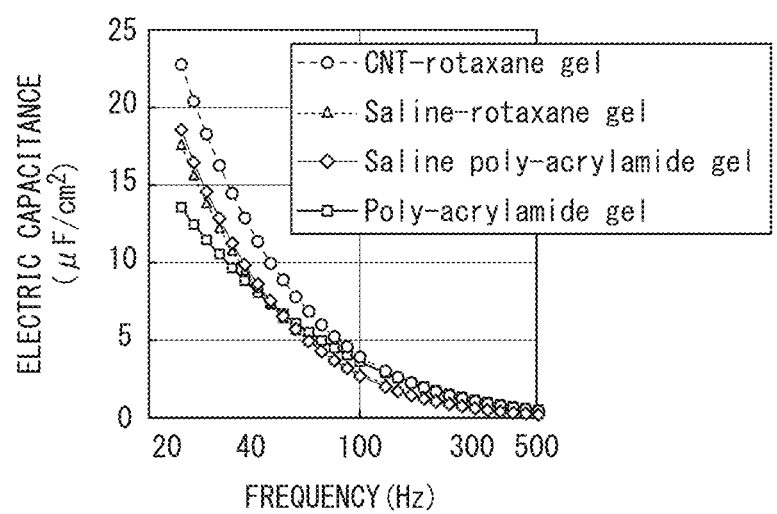
FIG. 11 is a graph showing an electric capacitance of the invention (or conductive material) and frequency dependency thereof.

FIG. 11 is a graph showing an electric capacitance of the composition (CNT-rotaxane gel) which is an embodiment of the invention and frequency dependency thereof. For comparison, graphs of a poly-acrylamide gel, a saline poly-acrylamide gel, and a saline-rotaxane gel are also shown.

The composition (CNT-rotaxane gel) is a composition obtained under the same conditions as the conditions for producing the composition shown in FIG. 8A. It has a size of 1 cm by 1 cm and a thickness of 1 mm.

The poly-acrylamide gel was obtained by mixing 1 mg of a photo-crosslinking agent with 300 mg of polyacrylamide, dissolving the mixture with 100 ml of deionized water, and then performing photo-crosslinking by UV. It has a size of 1 cm by 1 cm and a thickness of 1 mm.

The mixture may also be dissolved with 100 ml of a saline solution in place of the deionized water. In this case, the time and effort for substituting the water which is impregnated into the gel with the saline solution may be omitted and this may be applied to an organism.

The saline poly-acrylamide gel was obtained by mixing 1 mg of a photo-crosslinking agent with 300 mg of polyacrylamide, dissolving the mixture with 100 ml of a saline solution, and then performing photo-crosslinking by UV. It has a size of 1 cm by 1 cm and a thickness of 1 mm.

The saline-rotaxane gel was obtained by mixing 1 mg of a photo-crosslinking agent with 300 mg of a rotaxane gel, dissolving the mixture with 100 ml of a saline solution, and then performing photo-crosslinking by UV. It has a size of 1 cm by 1 cm and a thickness of 1 mm.

As shown in FIG. 11, it was found that the electric capacitance of the composition which is an embodiment of the invention is higher than those of the gels of the comparison examples.

When an electric signal is detected by capacitive coupling, its intensity is proportional to the surface area of the electrode. When an electrode is formed using the composition of the invention and used to detect an electric signal by capacitive coupling, the composition of the invention is very soft compared to a conventional metal electrode and the electrode can thus be exactly attached to biological tissues. Thus, the substantial contact area is increased. Therefore, the detection sensitivity of substantial capacity for obtaining an electric signal is extremely high compared to a conventional metal electrode, and even when the electrode has a smaller size, it has a high detection capability.

The composition or the conductive material of the invention contains a carbon nanomaterial, and since the carbon nanomaterial, especially carbon nanotubes, has a high specific surface area, it has a high signal detection capability. The conductivity of an electrode produced using the composition or the conductive material of the invention is lower than the conductivity of an Au electrode. However, when a signal is taken by capacity, it is not the conductivity that is important but a large effective surface area.

Hereinafter, a method of manufacturing a conductive material which is an embodiment of the invention will be described using FIG. 12 with an example in which carbon nanotubes are used as a carbon nanomaterial, N,N-diethyl-N-methyl-N-(2-methoxyethyl)ammonium tetrafluoroborate ($DEMEBF_4$) is used as an ionic liquid, and polyrotaxane is used as a water-soluble polymer.

(1) First Process

First, carbon nanotubes, $DEMEBF_4$, and water are mixed and stirred to obtain a first dispersion system in which the carbon nanotubes covered with molecules of the ionic liquid are dispersed.

A process of rinsing the first dispersion system with a saline solution, ethanol, a liquid which does not destroy the gel or the like may be performed to remove $DEMEBF_4$ which is not bonded to the carbon nanotubes.

In this dispersion system, the carbon nanotubes covered with the molecules of the ionic liquid are dispersed in the water. Depending on the amount of the carbon nanotubes and the ionic liquid, carbon nanotubes which are not sufficiently covered or not covered at all with the molecules of the ionic liquid (also including bundled carbon nanotubes) and the molecules of the ionic liquid may be contained.

In this process, it is preferable to apply a shearing force to the carbon nanotubes with a jet mill or the like to perform fragmentation. This is because, by virtue of this process, the carbon nanotubes bundled with a van der Waals force are released one by one, and thus the degree of bundling (aggregation) can be reduced and the carbon nanotubes can be released one by one.

Figure 14:
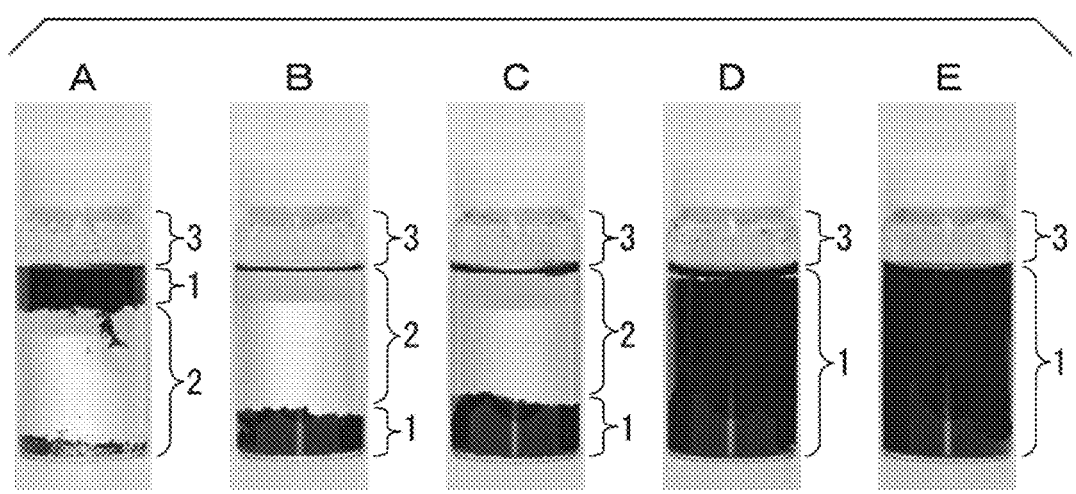
FIG. 14 is a photograph showing results of the examination of dispersibility of carbon nanotubes. (A) is a photograph showing a state after stirring carbon nanotubes in deionized water for a week, (B) is a photograph showing a state after similarly stirring carbon nanotubes and $DEMEBF_4$ in deionized water for a week, (C) is a photograph showing a state after similarly stirring carbon nanotubes in deionized water for a week and then processing the resulting material with a jet mill, (D) is a photograph showing a state after similarly stirring carbon nanotubes and 60 mg of $DEMEBF_4$ in deionized water for a week and then processing the resulting material with a jet mill, and (E) is a photograph showing a state after a paste obtained by similarly stirring carbon nanotubes, $DEMEBF_4$, and microfibrillated cellulose in deionized water for a week is processed with a jet mill.

FIG. 14 shows results of the examination of dispersibility of carbon nanotubes. (A) shows a state after stirring 30 mg of carbon nanotubes in deionized water at 25° C. using a magnetic stirrer at 700 rpm or higher for a week, (B) shows a state after similarly stirring 30 mg of carbon nanotubes and 60 mg of $DEMEBF_4$ in deionized water at 25° C. for a week, (C) shows a state after similarly stirring 30 mg of carbon nanotubes in deionized water at 25° C. for a week and then processing the resulting material with a high-pressure jet milling homogenizer (60 MPa; Nano-jetpal, JN10, Jokoh), (D) shows a state after similarly stirring 30 mg of carbon nanotubes and 60 mg of $DEMEBF_4$ in deionized water at 25° C. for a week and then processing the resulting material with a high-pressure jet milling homogenizer, and (E) shows a state after a paste obtained by similarly stirring 30 mg of carbon nanotubes, 60 mg of $DEMEBF_4$, and microfibrillated cellulose (100 mg of a 10% cellulose-containing solution, "CELISH (product name)", manufactured by Daicel Chemical Industries, Ltd.) in deionized water at 25° C. for a week is processed with a high-pressure jet milling homogenizer. These are photographs taken after a week from the termination of the stirring. In these photographs, the black portions 1 indicate a layer including carbon nanotubes, the white-looking portions 2 indicate a layer of deionized water, and the transparent portions 3 indicate cavity. The "CELISH (product name)" is cellulose nanofiber microfibrillated by a special processing method, and is produced from highly refined, pure vegetable fiber raw materials. The raw material fiber is unraveled into tens of thousands of strands by this process and the fiber thickness is refined to 0.1 μm to 0.01 μm.

From (D) and (E), it is found that the carbon nanotubes have high dispersibility in the water. It is found that to obtain high dispersibility, it is preferable to fragment the bundled carbon nanotubes by applying a shearing force.

(2) Second Process

Next, the first dispersion system, polyrotaxane ("photo-crosslinkable slide-ring gel", manufactured by Advanced Softmaterials Inc.), and water are mixed and stirred to obtain a second dispersion system in which the carbon nanomaterial covered with the molecules of the ionic liquid and the water-soluble polymer are dispersed.

A process of rinsing the second dispersion system with a saline solution, ethanol, a liquid which does not destroy the gel or the like may be performed to remove the $DEMEBF_4$ which is not bonded to the carbon nanotubes.

Figure 12:
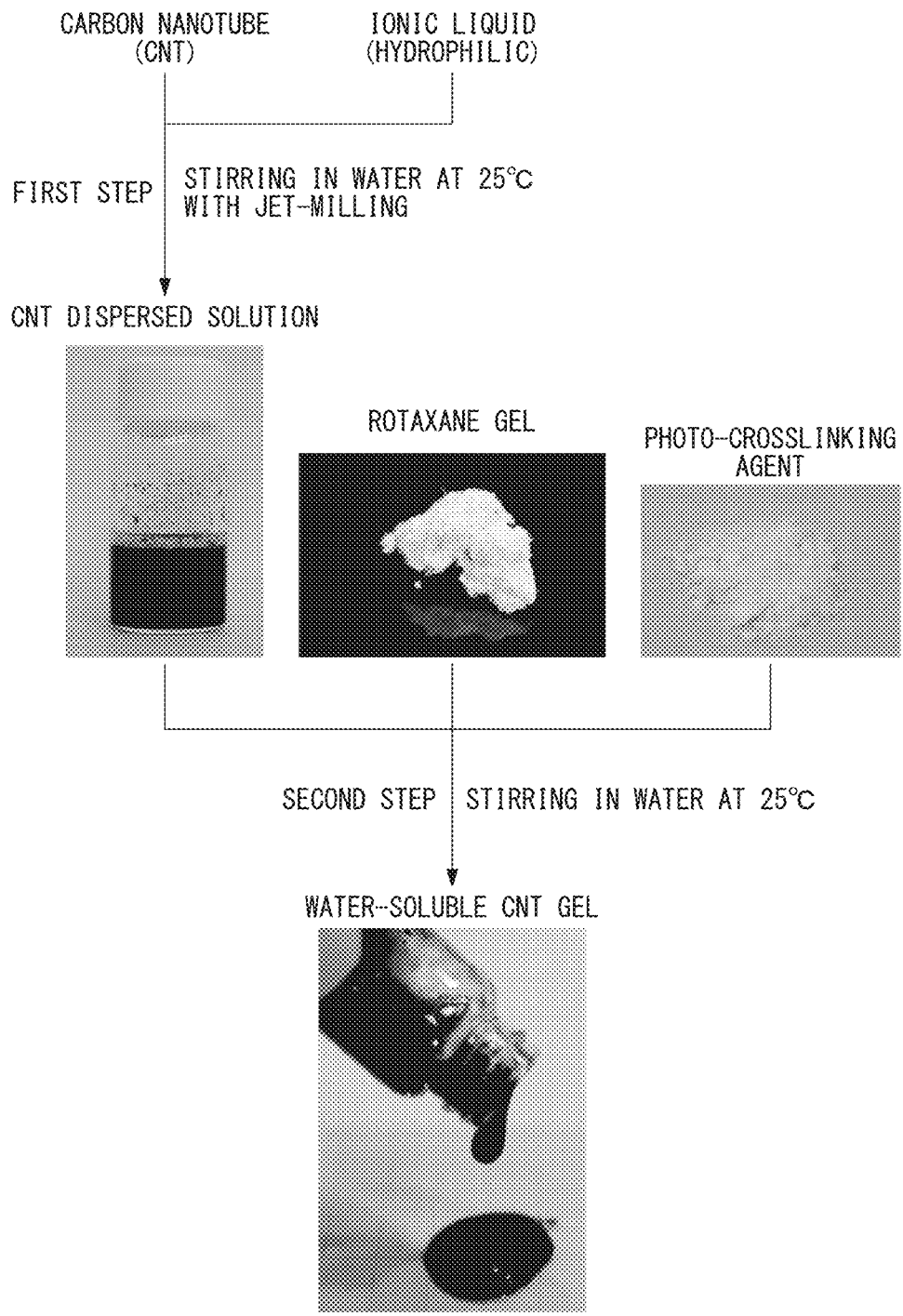
FIG. 12 is a flow diagram for illustrating a method of manufacturing the conductive material of the invention.

As shown in FIG. 12, a crosslinking agent may be mixed when crosslinking the obtained composition. Accordingly, the obtained second dispersion system is a gel-like substance as shown in FIG. 12.

(3) Crosslinking Process

Next, by crosslinking the polyrotaxane, a composition (conductive material) in which the carbon nanotubes covered with the molecules of the $DEMEBF_4$ are dispersed in the polyrotaxane medium and the polyrotaxane is crosslinked is obtained.

A process of rinsing the obtained composition (conductive material) with a saline solution, ethanol, a liquid which does not destroy the gel or the like may be performed to remove the $DEMEBF_4$ which is not bonded to the carbon nanotubes.

By virtue of the above processes, the composition (conductive material) according to an embodiment of the invention can be obtained.

Next, an example of a process of forming a sheet formed of the composition (conductive material) according to an embodiment of the invention and a line with a fine line width formed of the composition (conductive material) according to an embodiment of the invention using the second dispersion system will be described.

Figure 13:
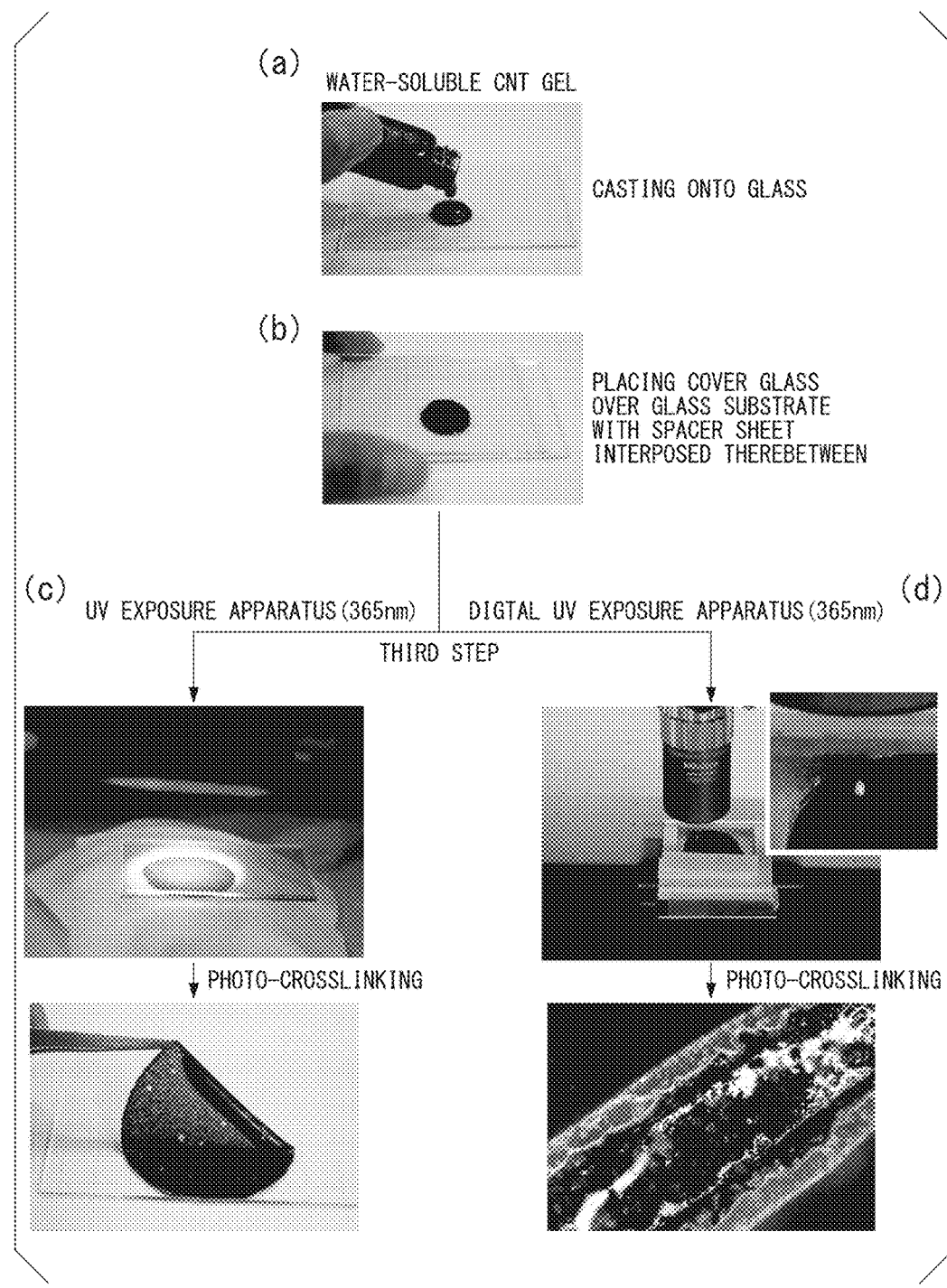
FIG. 13 is a flow diagram showing an example of the application of the method of manufacturing the conductive material of the invention.

As shown in FIG. 13(a), the second dispersion system is cast (flow casting) on a glass substrate. Next, as shown in FIG. 13(b), a cover glass is placed on the glass substrate via a spacer sheet having a desired thickness (50 μm in the example of FIG. 13(b)).

Next, when a sheet is produced, a sheet having a thickness of 50 μm can be obtained by, for example, exposure using an ultraviolet (365 nm) exposure device as shown in FIG. 13(c). When a line with a fine line width is formed, for example, a line having a width of 50 μm can be formed by exposure using, for example, a digital ultraviolet (365 nm) exposure device as shown in FIG. 13(d).

The embodiments of the invention have been described as above, but the invention is not limited to the above-described embodiments, and various modifications may be made without departing from the gist of the invention.

For example, in the above-described embodiments, the signal detectors F11 to F88 are uniformly arranged in a matrix, but these may be nonuniformly arranged according to the shape of a subject. In addition, an output signal $S_{out}$ of the amplifier 103 is taken as a voltage signal, but the invention is not limited to this example and the output signal $S_{out}$ may be taken as a current signal.

In the example of FIG. 5, the capacitor 102 is formed of the metal layer 2012, the $AlO_x$/SAM layer 2013, and the metal layer 2014. However, for example, the metal layer 2012, the $AlO_x$/SAM layer 2013, and the metal layer 2014 may be omitted and the capacitor 102 may be formed of the conductive layer 204, the polyimide layer 2011, and the conductive gel layer 2015. In addition, the metal layer 2029, the conductive layer 204, the metal layer 2016, and the polyimide layer 2011 may be omitted, the metal layer 2012 may be directly formed on the parylen layer 2027, and the capacitor 102 may be formed of the metal layer 2012, the $AlO_x$/SAM layer 2013, and the metal layer 2014. Various organic films, inorganic films, lamination films of organic films and inorganic films can be used as the insulating layer (dielectric layer) of the capacitor 102. Particularly, parylen is effectively used for improving the sealing performance. When a laminated structure is made in which a thin film having a more excellent moisture/oxygen barrier property is formed on the surface of the polyimide layer 2011 or another flexible base, the sealing performance can be further improved. For example, inorganic films such as a parylen film, a silicon oxide film ($SiO_x$), and a silicon nitride film (SiN) and lamination films of the inorganic films and organic films are effective as the thin film.

INDUSTRIAL APPLICABILITY

According to the invention, it is possible to provide a signal detection device and a signal detection method indicating an excellent signal to noise ratio. It is possible to provide a signal detection device having excellent flexibility. It is possible to provide a signal detection device and a signal detection method having biocompatibility. It is possible to provide a signal detection device and a signal detection method adapted to detect a signal generated from an arbitrary object including industrial products.

REFERENCE SIGN LIST

100: SIGNAL DETECTION DEVICE
101: ELECTRODE
102: CAPACITOR
103: AMPLIFIER
1031 to 1034: TRANSISTOR
1035: RESISTANCE ELEMENT
201: ELECTRODE CIRCUIT LAYER
202: AMPLIFIER CIRCUIT LAYER
203: TRANSFER CIRCUIT LAYER
204, 205: CONDUCTIVE LAYER
F11 to F88: SIGNAL DETECTOR
T11 to T88: TRANSISTOR FOR SIGNAL TRANSFER
WL1 to WL8: WORD LINE
BL1 to BL8: BIT LINE

What is claimed is:

1. A signal detection device which detects a signal generated from a subject, the device having a Young's modulus of less than 1 kPa and comprising a laminated structure of:
   a first circuit layer in which a plurality of electrodes brought into contact with the subject is formed;
   a second circuit layer in which a plurality of amplifiers having an input portion capacitively coupled to the plurality of electrodes, respectively, is formed; and
   a third circuit layer in which a plurality of transistors for reading outputs of the plurality of amplifiers is formed;
   wherein an insulating layer which seals the second circuit layer is formed between the plurality of electrodes formed in the first circuit layer and the second circuit layer, and the plurality of electrodes and the input portions of the plurality of amplifiers are capacitively coupled to each other through the insulating layer, and wherein the first circuit layer and the second circuit layer, and the second circuit layer and the third circuit layer, are each electrically connected through a conductive sheet, wherein the first circuit layer and the third circuit layer have a same bending rigidity.

2. The signal detection device according to claim 1, wherein the electrode is made of a conductive material in which a carbon nanomaterial doubly covered with molecules constituting a hydrophilic ionic liquid and a water-soluble polymer is dispersed in a water-soluble polymer medium and the water-soluble polymer is crosslinked.

3. The signal detection device according to claim 1, wherein wiring for reading output signals of the plurality of amplifiers formed in the second circuit layer through the plurality of transistors formed in the third circuit layer is drawn to one side of the third circuit layer opposite the other side on which the second circuit layer is positioned.

4. The signal detection device according to claim 3, wherein the wiring is drawn to the one side of the third circuit layer in an outer circumferential region of the third circuit layer.

5. The signal detection device according to claim 1, wherein a plurality of capacitors is formed in the first circuit layer to capacitively couple the plurality of electrodes formed in the first circuit layer and input portions of the plurality of amplifiers formed in the second circuit layer.

6. The signal detection device according to claim 1, wherein the first circuit layer and the second circuit layer, and the second circuit layer and the third circuit layer, are each electrically connected through an anisotropic conductive sheet.

7. The signal detection device according to claim 1, wherein a member constituting the first circuit layer forms a sealing layer which seals the second circuit layer.

8. The signal detection device according to claim 1, wherein the second circuit layer is interposed between the first circuit layer and the third circuit layer, and thus the first circuit layer, the second circuit layer, and the third circuit layer are laminated, and the first circuit layer and the third circuit layer have the same bending rigidity.

9. A signal detection method of detecting a signal from the subject by using the signal detection device according to claim 1, the method comprising the step of:

selectively reading output signals of any of the plurality of amplifiers formed in the second circuit layer through the plurality of transistors formed in the third circuit layer.

10. The signal detection method according to claim 9, wherein the step of selectively reading output signals of any of the plurality of amplifiers formed in the second circuit layer includes a first step of scanning and sequentially reading output signals of the plurality of amplifiers through the plurality of transistors, a second step of generating a strength distribution of the output signals of the plurality of amplifiers read in the first step, and a third step of simultaneously reading one or more output signals of the plurality of amplifiers specified based on the result of the analysis of the strength distribution.

11. The signal detection device according to claim 1, wherein the second circuit layer and the third circuit layer are separated from the plurality of electrodes by an A10x/SAM layer.

* * * * *